US012595458B2

(12) United States Patent
Nothelfer et al.

(10) Patent No.: US 12,595,458 B2
(45) Date of Patent: Apr. 7, 2026

(54) DEVICE AND METHOD FOR DETERMINING A VIABILITY AND/OR A CELL COUNT OF BIOLOGICAL CELLS IN A SUSPENSION BY MEANS OF COLLIMATED TRANSMISSION

(71) Applicants: Sartorius Stedim Biotech GmbH, Göttingen (DE); Stiftung für Lasertechnologien in der Medizin und Meßtechnik an der Universität Ulm (Stiftung Bürgerliches Recht), Ulm (DE)

(72) Inventors: Steffen Nothelfer, Nersingen (DE); Alwin Kienle, Blaustein (DE); Florian Foschum, Neu-Ulm (DE); Marek Hoehse, Göttingen (DE)

(73) Assignees: Sartorius Stedim Biotech GmbH (DE); Stitftung für Lasertechnologien in der Medizin und Me technik an der Universität Ulm, Ulm (DE)

( * ) Notice: Subject to any disclaimer, the term of this patent is extended or adjusted under 35 U.S.C. 154(b) by 643 days.

(21) Appl. No.: 17/925,897

(22) PCT Filed: May 3, 2021

(86) PCT No.: PCT/EP2021/061518
§ 371 (c)(1),
(2) Date: Nov. 17, 2022

(87) PCT Pub. No.: WO2021/233664
PCT Pub. Date: Nov. 25, 2021

(65) Prior Publication Data
US 2023/0183635 A1     Jun. 15, 2023

(30) Foreign Application Priority Data

May 20, 2020    (EP) ..................................... 20175682

(51) Int. Cl.
*C12M 3/00*        (2006.01)
*B01L 3/00*        (2006.01)
(Continued)

(52) U.S. Cl.
CPC ............ *C12M 41/46* (2013.01); *C12M 41/36* (2013.01)

(58) Field of Classification Search
CPC .............................. C12M 41/36; C12M 41/46
See application file for complete search history.

(56) References Cited

U.S. PATENT DOCUMENTS 5,356,815 A      10/1994  Ciotti
5,589,932 A  *  12/1996  Garcia-Rubio ........ G01N 21/31
                                                              356/39

(Continued)

FOREIGN PATENT DOCUMENTS

CN          110358684 A      10/2019

OTHER PUBLICATIONS

English translation of CN 110358684 to Feng et al, generated 2025.*

(Continued)

*Primary Examiner* — Nathan A Bowers
(74) *Attorney, Agent, or Firm* — Klarquist Sparkman, LLP

(57) ABSTRACT

Devices and methods are provided for determining viability and/or a cell counts of biological cells in a cell suspension culture using collimated transmission. Devices can include an illumination source for generating an electromagnetic illumination beam; beam manipulation means for collimating the illumination beam; and a detection unit for detecting an electromagnetic transmission beam being a portion of the collimated illumination beam which has been transmitted through a sample of the cell suspension culture.

15 Claims, 11 Drawing Sheets

(51) Int. Cl.
    C12M 1/34        (2006.01)
    G01N 1/00        (2006.01)

(56) References Cited

U.S. PATENT DOCUMENTS

| | | | |
|---|---|---|---|
| 2005/0260741 A1 | 11/2005 | Albertson et al. | |
| 2008/0180664 A1* | 7/2008 | Backman | G01N 21/49 |
| | | | 356/317 |
| 2008/0262321 A1* | 10/2008 | Erad | G01N 35/00871 |
| | | | 422/52 |
| 2010/0032582 A1* | 2/2010 | Xia | G01N 21/6408 |
| | | | 250/458.1 |
| 2018/0228375 A1* | 8/2018 | Kim | G01N 33/582 |
| 2018/0348135 A1 | 12/2018 | Ingber et al. | |
| 2019/0219508 A1* | 7/2019 | Büchs | C12M 41/46 |

OTHER PUBLICATIONS

International Search Report and Written Opinion, mailed Jul. 6, 2021, issued for International Patent Application No. PCT/EP2021/061518, 11 pages.

* cited by examiner a)

b)

a)

b)

c)

a)

b)

a)

b)

c)

a)

b)

c)

a)

b)

DEVICE AND METHOD FOR DETERMINING A VIABILITY AND/OR A CELL COUNT OF BIOLOGICAL CELLS IN A SUSPENSION BY MEANS OF COLLIMATED TRANSMISSION

CROSS REFERENCE TO RELATED APPLICATIONS

This is the U.S. National Stage of International Application No. PCT/EP2021/061518, filed May 3, 2021, which was published in English under PCT Article 21 (2), which in turn claims the benefit of European Patent Application No. 20 175 682.2 filed May 20, 2020. The prior applications are incorporated herein by reference in their entirety.

The present invention relates to a device and method for determining a viability and/or a cell count of biological cells in a cell suspension culture by means of collimated transmission. Furthermore, the present invention relates to a bioreactor and the use of collimated transmission.

Conventionally, the determination of the viability or apoptosis, as used e.g. in upstream processes, is carried out by sampling and subsequent offline analysis. The offline analysis usually comprises staining of dead cells, e.g. with Trypan blue which is taken up only by the dead cells and actively excluded from live cells. Once the cells have been stained, they are counted, e.g. by using a flow cytometry or a hemocytometer. Then, a calculation is carried out to determine the original concentration of live cells.

Sampling with subsequent offline analysis, however, is insecure and also lacks reliability. Apart from an insufficient amount of data obtained from an offline analysis, taking a specimen is always associated with the risk of contamination (e.g. bacterial infection) and thus the discontinuation of an upstream process. Furthermore, offline analytics prevents complete monitoring of a bioprocess, which is particularly essential for a fully automated and regulated process.

In the biopharmaceutical production, sampling to determine viability and cell concentration is usually carried out only once a day, making an automated, regulated process impossible. Especially with Fed batch cultures, however, an inline analysis that allows a regulated process would be desirable. Particularly for perfusion processes, such an inline analysis would be advantageous. Although promising approaches using Raman spectroscopy have been suggested, Raman spectroscopy is technically complex and expensive.

Thus, it is a problem of the present invention to provide a device and method that allow a simple, cheap and reliable inline analysis of biological cells in a cell suspension culture. This problem is solved by the subject-matter of the independent claims. Preferred embodiments are defined in the dependent claims.

According to one aspect of the present invention, a device for determining a viability and/or a cell count of biological cells in a cell suspension culture by means of collimated transmission is provided. The device comprises:
- an illumination source for generating an electromagnetic illumination beam;
- beam manipulation means for collimating the illumination beam; and
- a detection unit for detecting an electromagnetic transmission beam being a portion of the collimated illumination beam which has been transmitted through a sample of the cell suspension culture.

In cell biology and microbiology, the term "viability" denotes the proportion of living cells in a cell population. The number of dead cells and the number of living cells together give the total number of cells or the total cell count. Hence, the viability is the proportion of the living cells with respect to the total cell count. The cell count particularly comprises a viable cell count (i.e. a count of the viable cells in the cell suspension culture) and/or the total cell count (i.e. a count of the total number of cells in the cell suspension culture).

The device (measuring device) according to the present invention may be a sensor and/or probing head for use with or in a bioreactor. Alternatively, the device according to the present invention may be part of a bioreactor.

The illumination source may comprise or be a polychromatic light source (e.g. a halogen bulb) so that the illumination beam generated by the illumination source has a certain range of wavelengths. In particular, the illumination beam may have a spectral range of 200 nm to 1000 nm. Alternatively, the illumination source may comprise or be a monochromatic light source (e.g. a laser or a light emitting diode), wherein the wavelength of the illumination source is tuneable. For example, the illumination source may be a tuneable laser, or the illumination source may comprise at least two monochromatic light sources (e.g. light emitting diodes) with different wavelengths. In particular, the illumination source is configured to generate electromagnetic radiation of at least two different wavelengths, either simultaneously or subsequently.

The beam manipulation means may comprise one or more optical or electro-optical elements. In particular, the manipulation means may comprise illumination beam manipulating means for manipulating and/or collimating the illumination beam. Further, the manipulation means may comprise transmission beam manipulation means for manipulating the transmission beam. The illumination beam manipulation means may be arranged between the illumination source and the sample volume, and the transmission beam manipulation means may be arranged between the sample volume and the detection unit.

The detection unit may comprise or be a spectrometer. Alternatively, the detection unit may comprise or be a broadband detector or a tunable monochromatic detector. The detection unit may comprise at least one point detector (e.g. photo diode) or at least one array of detectors (e.g. CCD or CMOS). The detection unit is configured to detect the transmission beam which may have been manipulated by the manipulation means or transmission beam manipulation means.

The transmission beam is a portion or part of the collimated illumination beam which has passed or which has been transmitted through the sample of the cell suspension culture. In other words, the transmission beam substantially comprises electromagnetic radiation or light generated by the illumination source, which has not been scattered and absorbed by the cell suspension culture sample.

The sample of the cell suspension culture may be disposed or enclosed in a sample volume, i.e. a sample container. The sample volume or sample container may be part of the device or part of a bioreactor. The sample volume or sample container may be formed, e.g., as a slab. In particular, the sample or sample volume has a predetermined width through which the illumination beam can pass. Accordingly, the width of the sample or sample volume to be investigated is referred to as the transmission width.

By means of collimated transmission, the method and device according to the present invention allow to quantitatively measure an extinction coefficient, and thereby, to quantify the light scattering of the biological cells. Compared to conventional methods and devices, this enables a simple, cheap and reliable inline analysis of biological cells in a cell suspension culture.

In a preferred embodiment, the beam manipulation means are configured to manipulate the illumination beam and/or the transmission beam such that an effective acceptance angle $\theta_a$ of the collimated transmission is equal to or below a specified (predetermined or determinable) threshold value. The effective acceptance angle $\theta_a$ is particularly defined as the sum of:

a maximal illumination beam divergence angle $\theta_1$ (also referred to as illumination beam acceptance angle) of the collimated electromagnetic illumination beam, and a maximal transmission beam detection angle $\theta_2$ (also referred to as transmission beam acceptance angle) of the transmission beam.

The "effective acceptance angle" is particularly a measure for the degree of collimation. In particular, the lower the effective acceptance angle is, the better is the collimation, and/or the higher the effective acceptance angle is, the larger is a beam divergence of the illumination beam and/or the transmission beam.

It is noted that the "effective acceptance angle", the "divergence angle" and the "detection angle", as used within the present description, are well known quantities that are related to the numerical aperture NA. The numerical aperture NA of an optical system is a dimensionless number that characterizes the range of angles over which the system can accept or emit light. In the present case, the device may be separated into two systems, namely an illumination system and a transmission system. Accordingly, the illumination beam divergence angle $\theta_1$ may be related to an illumination numerical aperture NA, of the illumination system, and the transmission beam detection angle $\theta_2$ may be related to a transmission numerical aperture $NA_2$ of the transmission system. Further, the effective acceptance angle $\theta_a$ is related to an effective numerical aperture $NA_{eff}$.

Generally, the numerical aperture is given by NA=n sin θ, where n is the index of refraction of the medium in which a lens is working, and θ is the maximal half-angle of the cone of light that can enter or exit the lens. In general, this is the angle of the real marginal ray in the optical system. Thus, in the present case, the relationships between the angles $\theta_1$, $\theta_2$ and $\theta_a$ on the one hand and the numerical apertures $NA_1$, $NA_2$ and $NA_{eff}$ on the other hand may be defined as follows:

$$NA_1 = n_1 \sin \theta_1,$$

$$NA_2 = n_2 \sin \theta_2, \text{ and}$$

$$NA_{eff} = n_{eff} \sin \theta_a,$$

where $n_1$ is an index of refraction of the illumination system, $n_2$ is an index of refraction of the transmission system, and $n_{eff}$ is an effective index of refraction of the total system (i.e. the whole device).

Moreover, it is noted that in light scattering theory, the extinction coefficient is defined by means of a wave theory, for which the beam shape or detectable wave space is a superposition of k-vectors with a certain width. This width exactly corresponds to the "divergence angle", the "detection angle" or the "acceptance angle", respectively.

In particular, the beam manipulation means are configured such that substantially only a part of the electromagnetic illumination beam, which is neither absorbed nor scattered by the sample is detected by the detection unit.

In a further preferred embodiment, the beam manipulation means are configured to collimate the illumination beam such that the illumination beam has a divergence angle of less than 1.5 degrees, and more preferably of less than 1.0 degree. In other words, the maximal illumination beam divergence angle $\theta_1$ is preferably 1.5 degrees and more preferably 1.0 degree. Alternatively or in addition, the beam manipulation means, particularly a transmission beam manipulation unit of the beam manipulation means, are/is configured to manipulate the transmission beam such that the transmission beam has a divergence angle of less than 1.5 degrees, and more preferably of less than 1.0 degree. In other words, the maximal transmission beam detection angle $\theta_2$ is preferably 1.5 degrees and more preferably 1.0 degree. Alternatively or in addition, the beam manipulation means are configured to manipulate the illumination beam and/or the transmission beam such that an effective acceptance angle $\theta_a$ of the collimated transmission is equal to or less than 3 degrees, more preferably less than 2 degrees, and most preferably less than 1.0 degree.

Within the present invention it has been found out that in turbid samples such as biological cell suspensions, an enlarged acceptance angle leads to a non-specific detection of light. In particular, an enlarged acceptance angle leads to a nonlinear mixture of light extinction due to absorption and scattering of the analyte, which makes model development based on multivariate methods very complex or even impossible. By reducing or limiting the effective acceptance angle, this nonlinear mixture, however, can be reduced and at a sufficiently small effective acceptance angle, the so-called extinction coefficient $\mu_t$ of Beer's law (Beer-Lambert law) can be determined from the transmission measurement. The extinction coefficient represents a linear sum of absorption and scattering, which makes model development possible. It is noted in this respect that commercial transmission probes in general allow to determine the absorption coefficient with a certain sensitivity to scattering, which strongly depends on the effective acceptance angle. For turbid media with small particles (isotropic scattering, g~0) the relation $\mu_a + \mu_s$ is still partially valid, but for cell suspensions, where the scattering is highly anisotropic (g~0.99 or even higher), state of the art transmission methods/probes detect a lot of scattered light, resulting in a very pronounced nonlinear mixture between scattering and absorption so that $\mu_a + \mu_s$ is absolutely invalid.

In a further preferred embodiment, the beam manipulation means comprise at least one of the following:

an illumination fiber (also referred to as source fiber) for guiding the illumination beam (particularly from the illumination source towards the sample);

an illumination beam collimation unit for collimating the illumination beam;

a transmission beam focusing unit for focusing the transmission beam;

a detection fiber for guiding the transmission beam to the detection unit.

In particular, the transmitted, not scattered and not absorbed part of the collimated incident beam is focused with the transmission beam focusing unit onto the detection fiber. Further, by means of the transmission beam focusing unit, the angles of the transmitted light which are being detected may be limited.

In a further preferred embodiment, the illumination fiber and/or the detection fiber have a numerical aperture smaller than 0.02. This results in an effective collimation and thus a sufficiently small effective acceptance angle.

In a further preferred embodiment, the illumination beam collimation unit and/or the transmission beam focusing unit comprises at least one of the following:

an aperture, a refractive focusing unit, and/or a reflective focusing unit.

The refractive focusing unit may comprise a focusing lens. The reflective focusing unit may comprise a mirror (e.g. a parabolic, toroid and/or ellipsoid mirror).

In a further preferred embodiment, the illumination beam collimation unit comprises an illumination fiber and an illumination focusing optics (comprising or being, e.g., an illumination lens), wherein the illumination fiber is configured to guide the illumination beam to the illumination focusing optics, wherein the illumination focusing optics is arranged between an end of the illumination fiber and the sample such that a distance between the end of the illumination fiber and the illumination focusing optics is equal to a focal length $f_1$ of the illumination focusing optics. Alternatively or in addition, the transmission beam focusing unit comprises a detection focusing optics (comprising or being, e.g., a detection lens) and a detection fiber, wherein the detection fiber is configured to guide the transmission beam to the detection unit, wherein the detection focusing optics is arranged between the sample and an end of the detection fiber such that a distance between the detection focusing optics and the end of the detection fiber is equal to a focal length $f_2$ of the detection focusing optics.

In a further preferred embodiment, the effective acceptance angle $\theta_a$ is given by the following equation:

$$\theta_a = \tan^{-1}\left(\frac{d_1}{f_1}\right) + \tan^{-1}\left(\frac{d_2}{f_2}\right),$$

where $d_1$ denotes an inner diameter of the illumination fiber, $d_2$ an inner diameter of the detection fiber, $f_1$ the focal length of the illumination focusing optics (e.g. an illumination lens), and $f_2$ the focal length of the detection focusing optics (e.g. a detection lens).

In a further preferred embodiment, the illumination source is a polychromatic light source, particularly with a spectral range of 200 nm to 1000 nm, and the detection unit is a spectrometer, particularly a digital spectrometer. Alternatively, the frequency of the illumination source is tuneable (i.e. the illumination source is particularly a tuneable light source), and the detection unit is a monochromatic detector (e.g. a photomultiplier tube or a photodiode). In both cases, it is possible to measure the extinction coefficient $\mu_t$ at least with light of two different wavelengths. In particular, it is possible to measure an extinction spectrum.

In a further preferred embodiment, the device further comprises an evaluation unit for determining the viability, a viable cell count and/or a total cell count of the biological cells based on the detected transmission beam. In particular, the evaluation unit is configured to determine an extinction spectrum based on the detected transmission beam and to determine the viability, the viable cell count and/or the total cell count based on the extinction spectrum. This can be done, e.g., by comparing the determined extinction spectrum with reference extinction spectra. The evaluation unit may comprise a processor and/or a computer. Determining an extinction spectrum in the sense of the present invention means determining the extinction coefficient $\mu_t$ for at least two different wavelengths $\lambda$ of the illumination beam. Preferably, extinction coefficients $\mu_t$ are determined for a plurality of different wavelengths $\lambda$. In particular, determining an extinction spectrum means determining an extinction coefficient curve in dependence of the wavelength $\lambda$ of the illumination beam.

In a further preferred embodiment, the reference extinction spectra are modelled based on first principles, particularly by solving the Maxwell's equations and/or using the Mie theory. Alternatively, the reference extinction spectra are obtained by measurements carried out on samples with predetermined and/or known properties such as vitality, viability, cell concentration, etc.

In a further preferred embodiment, the device comprises a sample container for containing the sample (to be investigated) of the cell suspension culture. In particular, the sample container is a slab.

According to a further aspect of the present invention, there is provided a bioreactor or biochemical reactor comprising a device for determining a viability and/or a cell count of biological cells in a cell suspension culture (i.e. a device according to the present invention).

According to a further aspect of the present invention, a method for determining a viability and/or a cell count of biological cells in a cell suspension culture by means of a collimated transmission is provided. The method comprises:

illuminating a sample of the cell suspension culture with a collimated electromagnetic illumination beam;

detecting an electromagnetic transmission beam being a portion of the collimated electromagnetic illumination beam which has been transmitted through the sample of the cell suspension culture; and determining the viability and/or the cell count of the biological cells based on the detected transmission beam.

Preferably, the illumination beam and/or the transmission beam are manipulated such that an effective acceptance angle of the collimated transmission is equal to or below a specified (predetermined or determinable) threshold value.

In a preferred embodiment, the illumination beam is collimated such that the illumination beam has a divergence angle of less than 1.5 degrees, and more preferably less than 1.0 degree. Alternatively or in addition, the transmission beam is manipulated such that the transmission beam has a divergence angle of less than 1.5 degrees, and more preferably less than 1.0 degree. Alternatively or in addition, the illumination beam and/or the transmission beam are manipulated such that the effective acceptance angle of the collimated transmission is equal to or less than 3 degrees, more preferably less than 2 degrees, and most preferably less than 1.0 degree.

A further aspect of the present invention relates to the use of collimated transmission for controlling bioprocesses. In particular, the controlling and/or monitoring may be carried out inline and/or in real-time.

A further aspect of the present invention relates to the use of the device and/or the method according to the present invention for controlling (particularly inline controlling or monitoring) a bioprocess.

The bioprocess may comprise or be a batch process, a fed-batch process, a continuous feed fed-batch process, a concentrated fed-batch process, a non-bleed perfusion process, and/or a perfusion process with cell bleed. In the following, the various upstream bioprocesses are briefly described:

Batch process: A single source of nutrients is the initial bioreactor filling (media) at batch start. No nutrients are added during the batch.

Fed-batch: During the cultivation nutrients are added. First, the nutrient level (most often glucose) is determined by sampling and offline reference. Based on the results the amount of feed is calculated (e.g. until a certain nutrient level is reached) and added to the bioreactor. In general, fed-batch processes are superior to batch processes as they allow longer process times, higher cell counts and higher titer levels.

Continuous Feed Fed batch: Contrary to normal fed-batches, the nutrients are not added as a (daily) bolus feed but continuously. This requires online measurement of nutrients. The nutrient profile follows a smooth line, contrary to the saw tooth wave of a fed batch with bolus feeds. Therefore, process conditions are more gentle as abrupt process changes are reduced.

Concentrated Fed-Batch: Used medium is constantly exchanged for fresh medium while the product is retained in the bioreactor. Thus, metabolites are removed from the process and fresh nutrients are provided while the product is concentrated. These results in higher viable cell densities and far higher product titer compared to fed-batch processes.

Perfusion without cell bleed: Used medium is constantly exchanged for fresh medium. Cells are retained in the vessel (using a cell retention device). By this, metabolites and/or cell toxic substances are removed from the process. The cells are retained in the bioreactor. With regard to process conduct, this is still considered a batch process as cell count continuously improves over process time.

Perfusion with Cell bleed: In addition to the previously described process of perfusion without cell bleed, cells and medium are removed (via a different channel as the standard medium exchange) from the bioreactor and fresh medium is added. After an initial growth phase, one reaches a plateau, a quasi-stationary process state in which there are no changes of the bioreactor composition over time. Depending on the measurement frequency of cell parameters, this quasi-stationary phase might resemble more to a sinus wave than a plateau. This process is also often referred to as continuous bioprocessing, even though the duration of these processes has only been realized for up to 2 months.

The device or sensor according to the present invention may be integrated in a bioreactor and detect at least one cell parameter (such as viability, viable cell count and/or total cell count) inline in real-time. For example, by means of or based on the device and/or method according to the present invention (i.e. by using collimated transmission), at least one cell parameter may be measured. Based on the measurement result, a pump (e.g. a feed pump or a cell bleed pump) used in the bioprocess may be controlled and/or adjusted. In particular, based on the measurement result, the pump may be activated (e.g. turned on) or deactivated (e.g. turned off). Alternatively or in addition, a pump speed of the pump may be adjusted (e.g. increased or decreased).

For example, particularly in case of a non-bleed perfusion process, the device and/or method according to the present invention, i.e. a corresponding measurement of at least one cell parameter carried out by the device of the present invention and/or according to the method of the present invention, may be used to determine or calculate a required nutrient level (e.g. based on a known cell specific nutrient consumption rate and a resulting cell specific perfusion rate). Based on the determined required nutrient level, a pump (e.g. a feed pump) may be controlled and/or adjusted.

Further, particularly in view of a perfusion process with cell bleed, a cell bleed may be controlled based on a measurement of at least one cell parameter by using the device and/or method according to the present invention. In particular, the at least one measured cell parameter may be compared with a specified set point or threshold. Based on the comparison result, a pump (e.g. a cell bleed pump) may be controlled and/or adjusted.

Using collimated transmission, and particularly using the device and/or method according to the present invention, for controlling a bioprocess results in an easier handling of the bioprocess and particularly allows an effective and reliable inline monitoring of cell parameters during the bioprocess.

For the above mentioned further independent aspect and in particular for preferred embodiments in this regard, the explanations given above or below concerning the embodiments of the first aspect also hold true. In particular, for one independent aspect of the present invention and for preferred embodiments in this regard, the explanations given above and below concerning the embodiments of the respective other aspects also hold true.

Individual embodiments for solving the problem are described by way of example below with reference to the figures. In this case, the individual embodiments described have in part features which are not absolutely necessary for implementing the claimed subject matter, but which provide desired properties in specific applications. In this regard embodiments which do not have all the features of the embodiments described below are also intended to be regarded as disclosed in a manner coming under the technical teaching described. Furthermore, in order to avoid unnecessary repetitions, specific features are mentioned only with regard to individual embodiments from among the embodiments described below. It is pointed out that the individual embodiments are therefore intended to be considered not only by themselves but also in a joint consideration. On the basis of this joint consideration the person skilled in the art will recognize that individual embodiments can also be modified by inclusion of individual or a plurality of features of other embodiments. It is pointed out that a systematic combination of the individual embodiments with individual or a plurality of features described with regard to other embodiments may be desirable and expedient and is therefore intended to be taken into account and also to be regarded as encompassed by the description.

BRIEF DESCRIPTION OF THE FIGURES

The above and other objects, features and advantages of the present invention will become more apparent upon reading of the following description of preferred embodiments and accompanying drawings. Other features and advantages of the subject-matter described herein will be apparent from the description and the drawings and from the claims. It should be understood that even though embodiments are separately described, single features and functionalities thereof may be combined without prejudice to additional embodiments. The present disclosure is illustrated by way of example and not limited by the accompanying figures.

Preferred embodiments of the present invention are exemplarily described regarding the following figures:

FIG. 4a shows a 3D model of CHO-K1 cells consisting of nucleus and cell body;

FIG. 4b shows the extinction spectrum of a CHO-K1 cell suspension, which is normalized to the concentration, with a viability of approximately 98%. The spectrum can be described using an analytical model based on the Mie theory and the geometry of living cells shown in FIG. 2a;

FIG. 4c shows the extinction spectrum of a CHO-K1 cell suspension with a viability of approximately 40%, where the spectrum cannot be described with an analytical Mie model based on a cell body and a nucleus as primary diffuser; The inlet on the right hand side is a microscopic image of a cell showing the typical fragmentation of the cell membrane at the onset of apoptosis;

Figure 8:
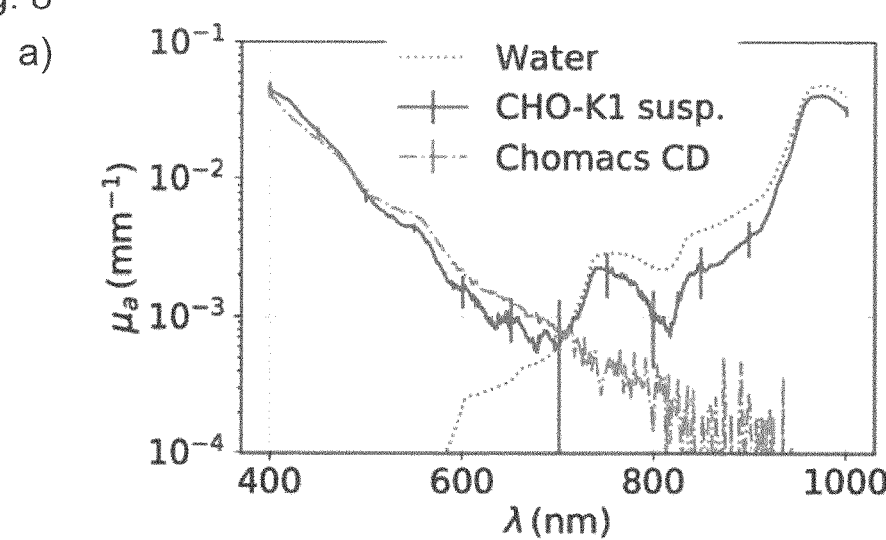
FIG. 8a shows absorption spectra of a CHO-K1 cell suspension from integrating sphere measurements.
FIG. 8b shows a reduced scattering spectrum (left axis) of a CHO-K1 cell suspension from integrating sphere measurements, as well as the extinction coefficient $\mu_t$ (right axis) of the same sample measured with collimated transmission.
FIG. 8c shows the anisotropy factor $$g = 1 - \frac{\mu_s'}{\mu_t - \mu_a}$$
Figure 8:
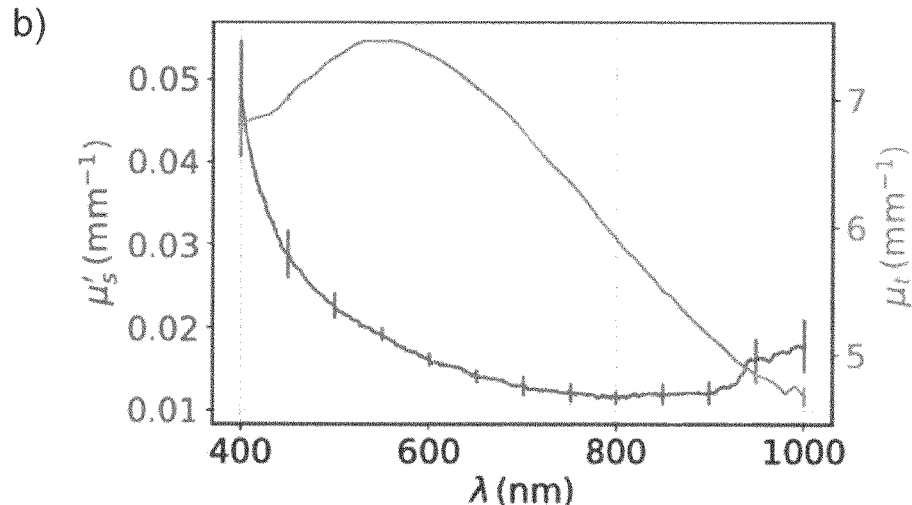
Figure 8:
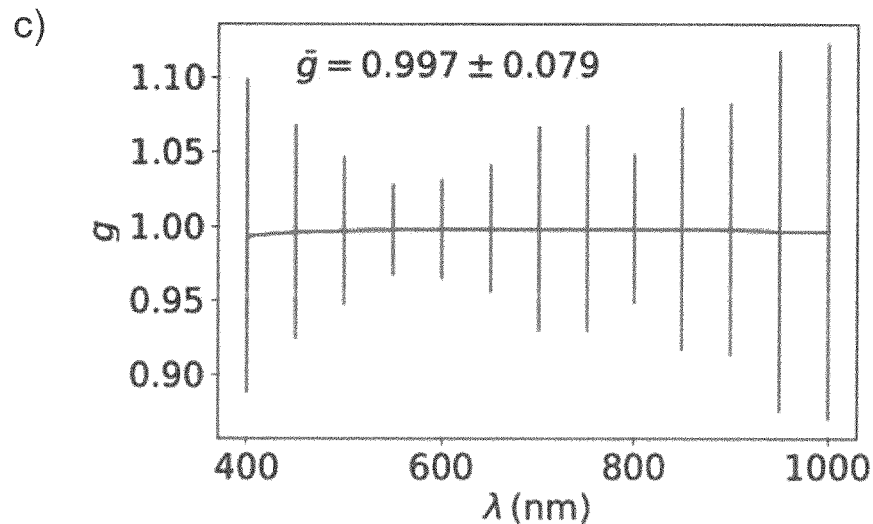
Figure 10:
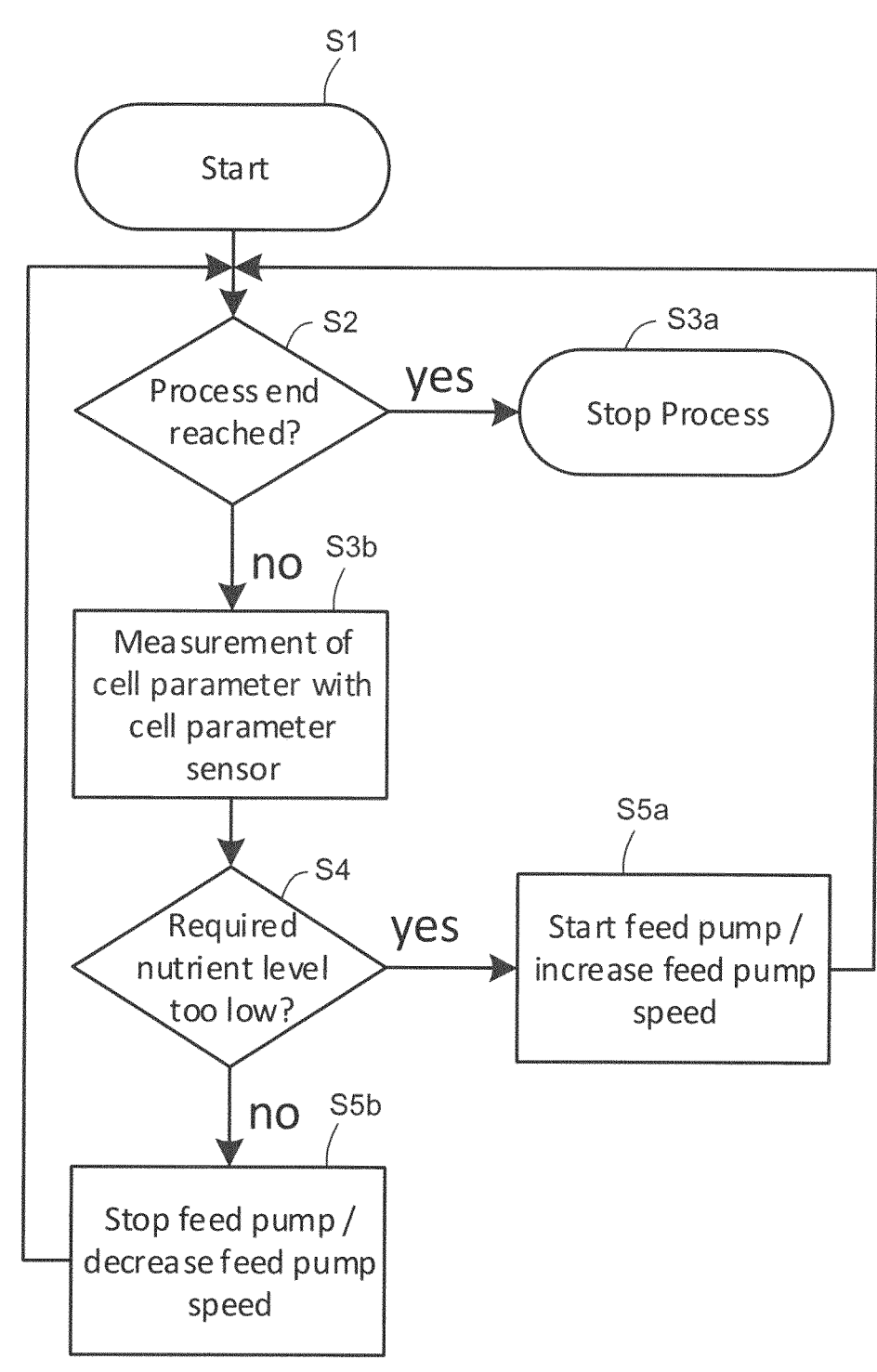
Figure 11:
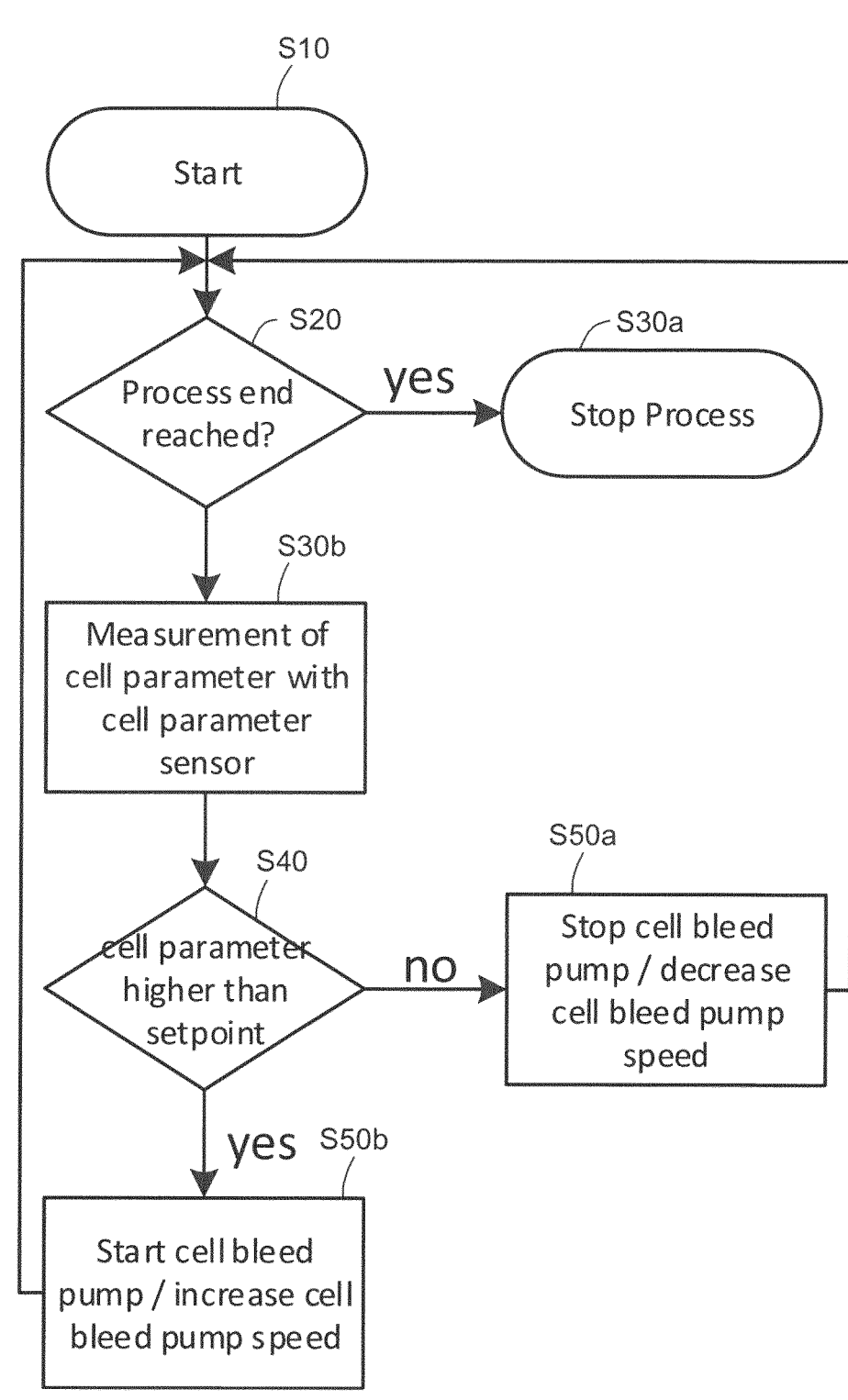

calculated from the integrating sphere and collimated transmission measurements shown in FIGS. 8a) and 8b);

FIG. 9a shows the cell concentration determined based on the absolute extinction coefficient in relation to a reference determined by the Neubauer-method;

FIG. 9b shows the cell viability predicted by an artificial neural network based on the extinction spectra, compared to a reference viability determined by the trypan blue coloring;

FIG. 10 shows a flow diagram of a non-bleed perfusion process according to an example; and FIG. 11 shows a flow diagram of a perfusion process with cell bleed according to an example.

DETAILED DESCRIPTION OF THE FIGURES

The following detailed description relates to exemplary embodiments of the present invention. Other embodiments of the invention are possible within the scope of the invention as defined by the appended claims. Throughout the figures, same reference signs are used for the same or similar elements.

Figure 1:
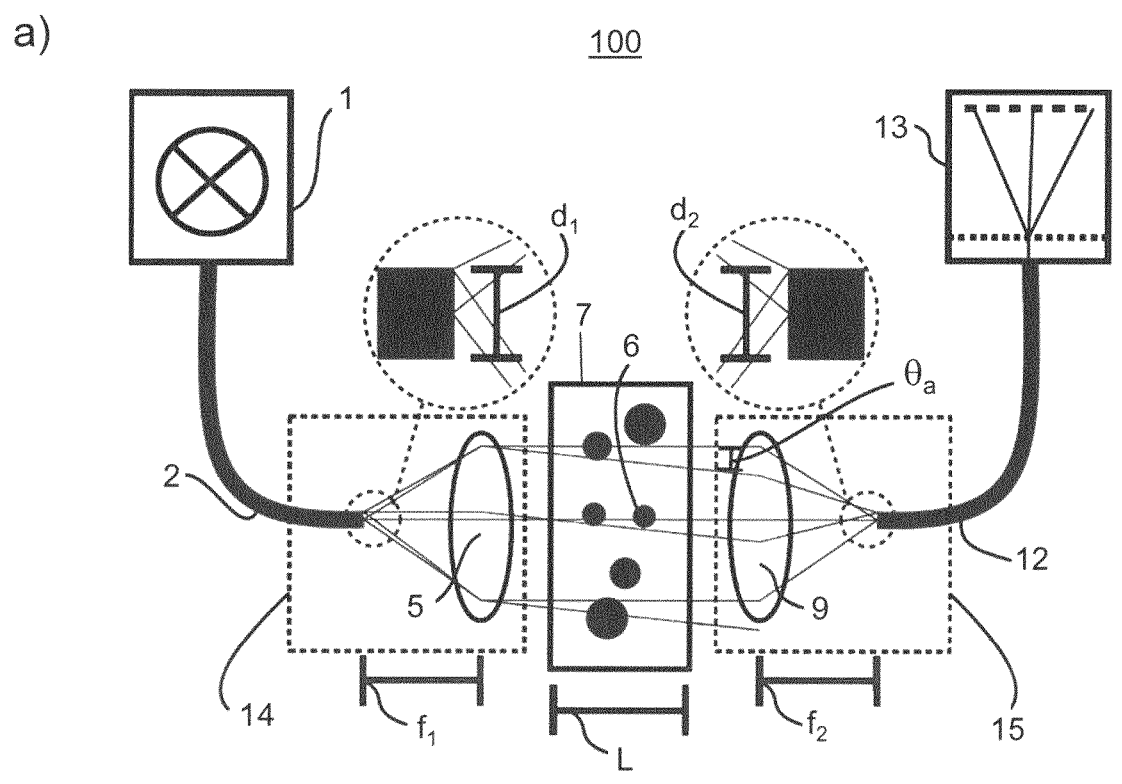
FIG. 1a shows a schematic representation of a device according to an example or an embodiment of the present invention.
FIG. 1b shows a schematic representation of a device according to a further example or embodiment of the present invention.
Figure 1:
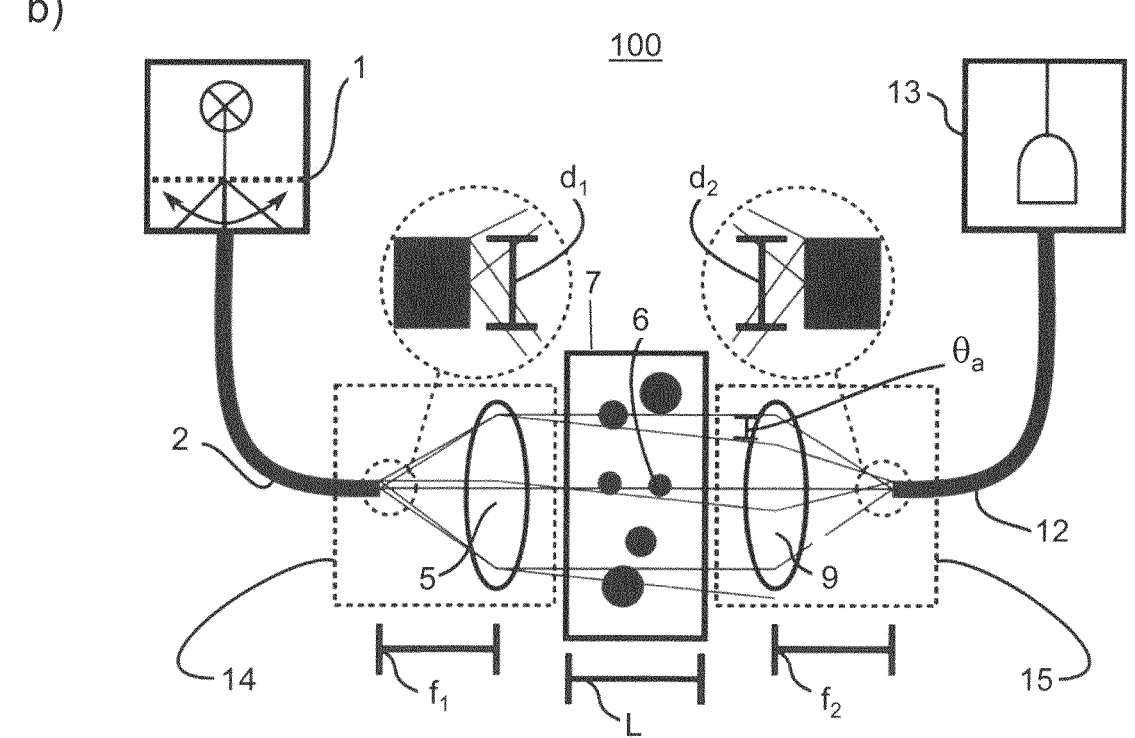

FIG. 1a shows a schematic representation of a setup or device 100 according to an embodiment of the present invention. The setup or device 100 is configured to measure the spectrally resolved extinction coefficient $\mu_t$ of light transmitting through a sample 6 by means of collimated transmission. The sample 6 comprises a suspension of biological cells (e.g. mammalian cells such as CHO-K1) of a bioreactor. Based on the spectrally resolved extinction coefficient $\mu_t$, it is possible to determine the viability, the viable cell count and/or the total (or absolute) cell count of the biological cells in the cell culture suspension. In particular, since a sample volume of the investigated or measured sample 6 is known, the concentration of the biological cells in the cell culture suspension may be determined. The sample 6 is contained in a container or slab 7, which may form a probe head of the device 100. Alternatively, the sample 6 may be contained in a sample volume or sample space of a bioreactor that may protrude from the bioreactor.

The device 100 comprises an illumination source 1 for generating an electromagnetic illumination beam and a detection unit 13 for detecting an electromagnetic transmission beam. The transmission beam is a portion of the collimated illumination beam which has been transmitted through the sample 6 of the cell suspension culture. In the embodiment of FIG. 1a, the illumination source 1 is a polychromatic light source and the detection unit 13 is a spectrometer.

Figure 2A:
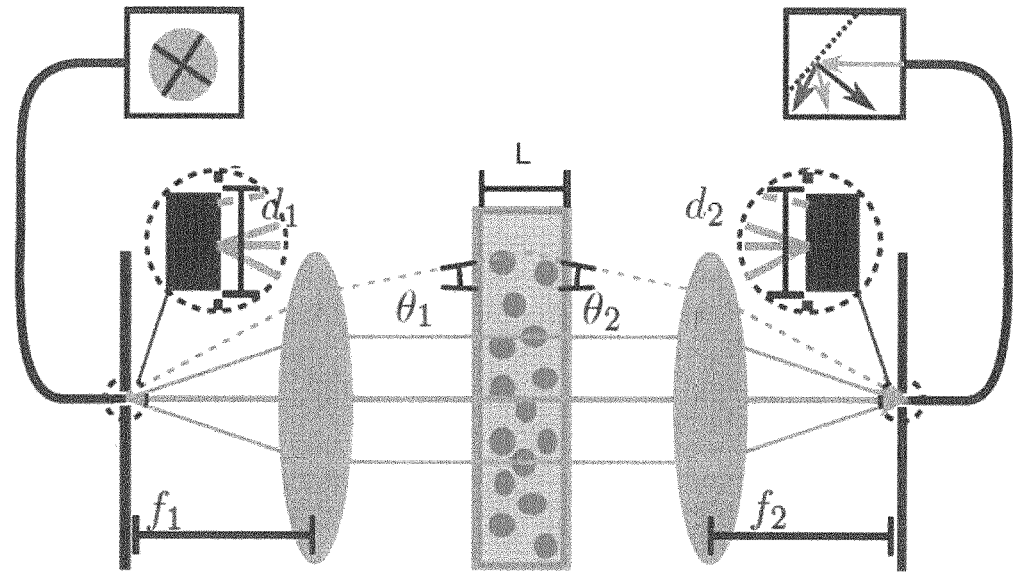
FIG. 2a shows a schematic representation of a device according to the embodiment of FIG. 1a, for illustrating an illumination beam divergence angle $\theta_1$ and a transmission beam detection angle $\theta_2$.

Moreover, the device 100 comprises beam manipulation means for manipulating the illumination beam and the transmission beam. According to the example of FIG. 1a, the beam manipulation means comprise an illumination fiber 2, an illumination lens 5, a detection lens 9 and a detection fiber 12. The beam manipulation means are configured to manipulate the illumination beam and/or the transmission beam such that an effective acceptance angle $\theta_a$ of the collimated transmission is equal to or below a specified (predetermined or determinable) threshold value. The effective acceptance angle $\theta_a$ is the sum of a maximal illumination beam divergence angle $\theta_1$ of the collimated electromagnetic illumination beam and a maximal transmission beam detection angle $\theta_2$ of the transmission beam (see FIG. 2a).

The beam manipulation means comprise an illumination beam collimation unit 14, wherein the illumination beam collimation unit 14 comprises the illumination fiber 2 and the illumination lens 5. The illumination fiber 2 is configured to guide the illumination beam to the illumination lens 5. The illumination lens 5 is arranged between an end of the illumination fiber 2 and the sample 6 (and/or the container

11

7) such that a distance between the end of the illumination fiber 2 and the illumination lens 5 is equal to a focal length $f_1$ of the illumination lens 5.

The beam manipulation means further comprise a transmission beam focusing unit 15, wherein the transmission beam focusing unit 15 comprises a detection lens 9 and a detection fiber 12. The detection fiber 12 is configured to guide the transmission beam to the detection unit 13. The detection lens 9 is arranged between the sample 6 (and/or the container 7) and an end of the detection fiber 12 such that a distance between the detection lens 9 and the end of the detection fiber 12 is equal to a focal length $f_2$ of the detection lens 9. Accordingly, illumination lens 5 and detection lens 9 are arranged in a Fourier arrangement and thus may be referred to as Fourier lenses.

The fiber coupled polychromatic light source 1 may have a spectral range of 200 nm to 1000 nm. The light coming from the source fiber 2, which may have an inner diameter of $d_1$=600 μm, is collimated by the focusing lens 5 with a focal length of, e.g., $f_1$=100 mm. The sample 6 is then illuminated by this collimated illumination light, and light which has neither been absorbed nor scattered is transmitted through the sample 6. A corresponding transmission length L through the sample 6 is defined by the sample volume or sample container 7. The transmitted light is then focused by a second lens (referred to as detection lens 9), with a focal length $f_2$ onto the end of a second fiber (referred to as detection fiber 12). The focal length $f_2$ of the detection fiber may be, e.g., 100 mm. For example, the detection fiber 12 has an inner diameter of $d_2$=1000 μm. Again, the detection fiber 12 is placed in the focal plane of the detection lens 9. The transmission light is guided to a digital spectrometer 13, which may for example be capable of acquiring spectra in the range of about 200 nm to 1000 nm. The spectrometer comprises, for example, a grating in combination with a diode array, wherein the grating serves as dispersive element for wavelength separation and the diode array serves as detector.

FIG. 1b shows a schematic representation of a device 100 for measuring the spectrally resolved extinction coefficient according to a further embodiment of the present invention. The only difference compared to the embodiment of FIG. 1a is that the illumination source 1 is a tunable light source (i.e., a frequency of the illumination source 1 is tuneable) and that the detection unit 13 is a monochromatic detector. The detector 13 may be a point, lines or array detector. The other parts are equivalent to the setup of FIG. 1a. For example, a spectrally resolved extinction coefficient and/or an extinction spectrum can be obtained by performing sequential measurements with illumination light of different wavelengths.

In particular, the following measurements are possible:
A) Using a polychromatic light source and a spectrometer on the detection side;
B) Performing sequential measurements (at least two) by tuning the wavelength of the light source and detecting the transmission beam with a photomultiplier tube or a photodiode;
C) Performing continued measurements with intensity modulation of different wavelengths (e.g. by modulating different colored LEDs) and detecting the transmission beam by a photomultiplier tube or a photodiode, combined with Fourier or continued wavelet transformation for separation of the different wavelengths. The transformations can either be done analog or digital, e.g. by Fast Fourier Transformation (FFT).

The embodiments of FIGS. 1a and 1b illustrate a possible realization for the measurement of the extinction coefficient at or in the bioreactor. The cell suspension of the bioreactor is illuminated with a small effective acceptance angle. In particular, in view the illumination beam manipulation unit 14, the effective acceptance angle can be limited by the ratio of focal length $f_1$ of the illumination lens 5 and diameter d1 of the illumination fiber 2. Correspondingly, in view the transmission beam manipulation unit 15, the effective acceptance angle can be limited by the ratio of focal length $f_2$ of the detection lens 9 and diameter $d_2$ of the detection fiber 12. Another possibility is to limit the effective acceptance angle by using an aperture and providing a certain distance between a distal end of the fiber and the aperture. Alternatively or in addition, a fiber with very low numerical aperture (NA<0.05) may be used.

The illumination beam divergence or deviation angle $\theta_1$ and the transmission beam detection or deviation angle $\theta_2$ are illustrated in FIG. 2a which again shows a schematic representation of a device 100 according to the embodiment of FIG. 1a. For the collimating units 14 and 15, the divergence or deviation angles $\theta_1$ and $\theta_2$ can be calculated by:

$$\theta_1 = \tan^{-1}\left(\frac{d_1}{f_1}\right); \quad \theta_2 = \tan^{-1}\left(\frac{d_2}{f_2}\right).$$

Thus, the combined or effective acceptance angle $\theta_a$, as illustrated in FIGS. 1a and 1b, is given by $$\theta_a = \theta_1 + \theta_2 = \tan^{-1}\left(\frac{d_1}{f_1}\right) + \tan^{-1}\left(\frac{d_2}{f_2}\right).$$

Figure 2B:
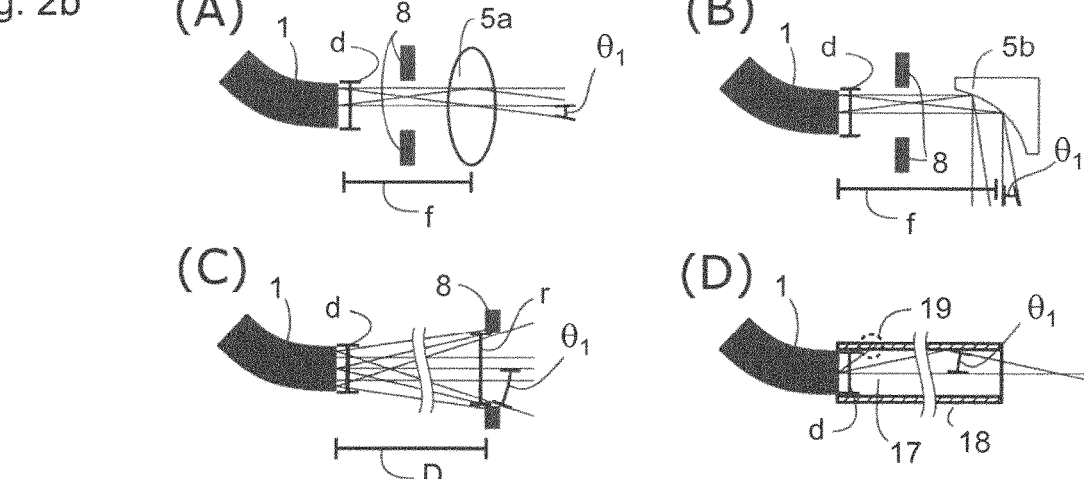
FIG. 2b shows schematic representations of four different principles (A), (B), (C) and (D) for limiting the effective acceptance angle.

FIG. 2b shows schematic representations of four different principles (A), (B), (C) and (D) that may be used for limiting the effective acceptance angle $\theta_a$. For each principle, it is assumed that light is coming from an electromagnetic light guide 1 with a certain core diameter d. According to principle (A), the beam diameter of the illumination beam exiting a distal end of the fiber 1 is reduced by an aperture 8 and a lens 5a is placed in a distance to the fiber, which corresponds to the focal length f of the lens 5a. According to principle (B), the beam diameter of the illumination beam exiting a distal end of the fiber 1 is reduced by an aperture 8, and a parabolic mirror 5b is placed in a distance to the fiber 1, which corresponds to the focal length of the parabolic mirror. According to principle (C), the beam divergence is limited by providing a distance D between the fiber 1 and an aperture 8. According to principle (D), the beam divergence is limited by the fiber 1 itself, namely by a refractive index difference between a core 17 of the fiber and a cladding 18 of the fiber. Light that is not totally reflected inside the fiber 1 is absorbed in the outer shell 19.

Thus, as illustrated in FIG. 2b, different designs for beam collimation relate to (A) a collimation by using a Fourier arrangement with transmission optics, (B) a Fourier arrangement with reflective optics, (C) a collimation by a certain distance between fiber and aperture, and/or (D) using a fiber with a very small numerical aperture (NA<0.02).

In particular, a small deviation angle can be achieved by the following technical solutions:
using an aperture and providing a distance $$D = \frac{r+d}{2}/\theta_1$$

between a distal end of the fiber and the aperture (where d is the fiber diameter and r is the aperture diameter);

using an aperture with diameter d in the focal plane of a focusing device, e.g. a lens with focal length f, wherein the focusing device is arranged in a distance f to the aperture (Fourier arrangement), and wherein the aperture is particularly formed by the inner diameter of a fiber;

using an electromagnetic radiation guide (e.g. a fiber or light guide) with a defined acceptance angle (e.g. a light guide with a very small refractive index step between the cladding and the core of the fiber, wherein the deviation angle is given by $$\theta_1 = \sin^{-1}\left(\frac{\sqrt{n_{core}^2 - n_{cladding}^2}}{n_{surrounding}}\right).$$

In case of a lens placed in air, $n_{surrounding}=1$.

Similar to collimating the illumination beam, also the detection may be carried out with a limited acceptance angle, e.g. an acceptance angle of smaller than 1.5°. The technical realization for this may be carried out in an analog way as illustrated in FIG. 2b for limiting the divergence angle of the incident electromagnetic illumination beam.

Thus, by means of the beam manipulation means, the incident electromagnetic illumination radiation has a limited divergence or deviation angle, particularly a divergence or deviation angle smaller than 1.5°. It is noted in this respect that typical fiber probes have a numerical aperture of NA>0.1 and therefore a deviation angle larger than 5°.

Moreover, the transmission path may have dynamically varying transmission lengths, which may be achieved, e.g., by using a mechanical moving stage. Also, different transmission path lengths may be provided in parallel, so that different lengths can be measured at once. A separation of length could be done, e.g., by means of a modulation with different frequencies or by sequentially closing and opening the transmission paths, e.g. by using one or more light switches (see FIG. 2c).

The optimal transmission path length depends on the light extinction of the analyte. In principle, a fixed transmission path could be used, but during cell growth (resulting, e.g., in an increase of cell concentration from $10^5$ cells/ml to $10^8$ cells/ml) the extinction also changes, and therefore, the detected signal may be reduced, e.g., by three orders of magnitude. The dynamic range of best state of the art spectrometers is big enough to measure such differences, but either signal to noise can be increased or cheaper devices can be used when different path lengths are measured. The simplest implementation is a multiple use of the design form FIGS. 1a and 1b. Alternatively, different path lengths can also be implemented in the same optical setup by including a device for blocking or modulating the different beam paths, herein referred to as a light switch. An example of such a "multi path" cuvette is shown in FIG. 2c.

Figure 2C:
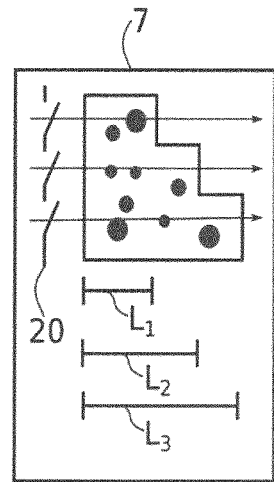
FIG. 2c shows a schematic representation of a cuvette with multiple transmission path lengths L1, L2 and L3, which can be controlled by light switches.

FIG. 2c shows a schematic representation of a container or cuvette 7 with multiple transmission path lengths L1, L2 and L3. The effective transmission path length of the cuvette 7 can be controlled by light switches 20. In the shown example, each transmission path is provided with a corresponding light switch 20. The light switch may be a simple mechanical shutter, a digital mirror device, a liquid crystal device or a more sophisticated acousto-optic modulator. Either a sequential measurement of the different paths or a modulation of the paths with different frequencies combined with a simultaneous detection is possible. In case of a simultaneous measurement, the subsequent separation could be done by Fast Fourier Transformation (FFT) or wavelet transformation.

In the following, a method for determining the viability, the viable cell count and/or the total cell count of biological cells such as CHO-K1 cells in suspension culture is described. The method is based on the measurement of collimated transmission of light (or electromagnetic radiation) through a slab filled with the cell suspension. Due to a difference in the refractive index between the biological cells and the surrounding medium, the light (or electromagnetic radiation) is scattered according to the scattering phase function of the biological cells into certain directions. However, due to the small contrast, i.e. the difference between the refractive index of cells (1.37) and the surrounding medium (1.34), the scattering of the cells is pronounced into forward direction, which results in an anisotropy factor g that is nearly one. If the effective acceptance angle $\theta_a$ which is the sum of the deviation angle $\theta_1$ of the incident light and the acceptance angle $\theta_2$ of the detection, is bigger than 1.0, the extinction coefficient may not reliably be measured, as scattered light will also fall into the aperture of the detector.

Figure 3:
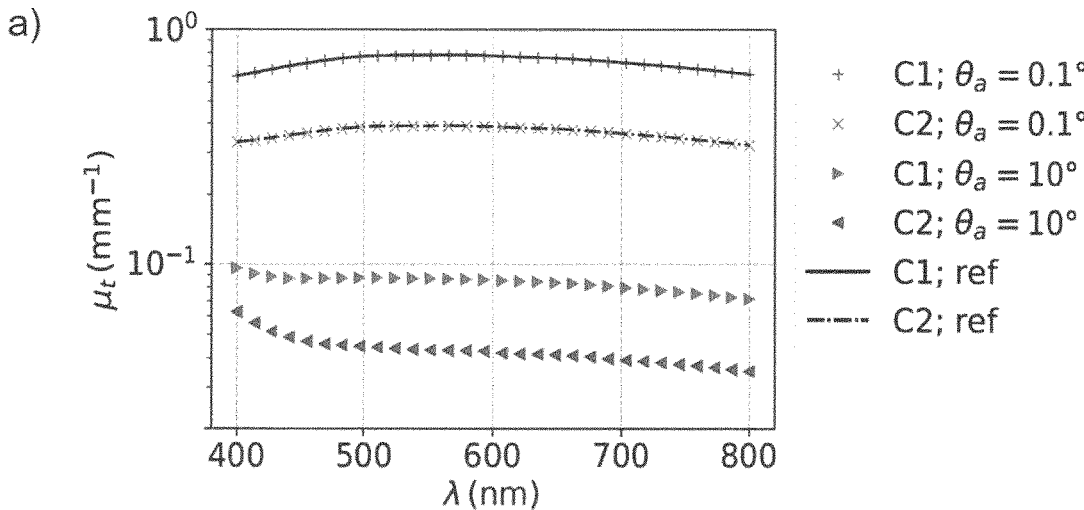
FIG. 3a shows simulated extinction spectra for two different concentrations C1 and C2 and two different effective acceptance angles 0.1° and 10°.
FIG. 3b shows simulated extinction spectra for different anisotropy factors g and two different effective acceptance angles 0.1° and 10°.
FIG. 3c shows simulated transmission coefficients $\mu_t$ with respect to actual transmission coefficients $\mu_{t,in}$ for different effective acceptance angles $\theta_a$ and for an anisotropy factor of 0.98.
Figure 3:
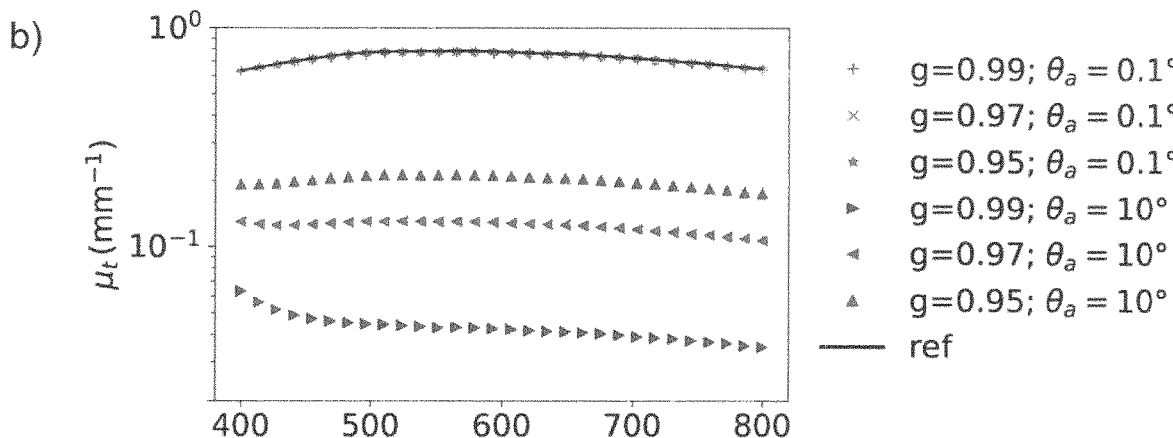
Figure 3:
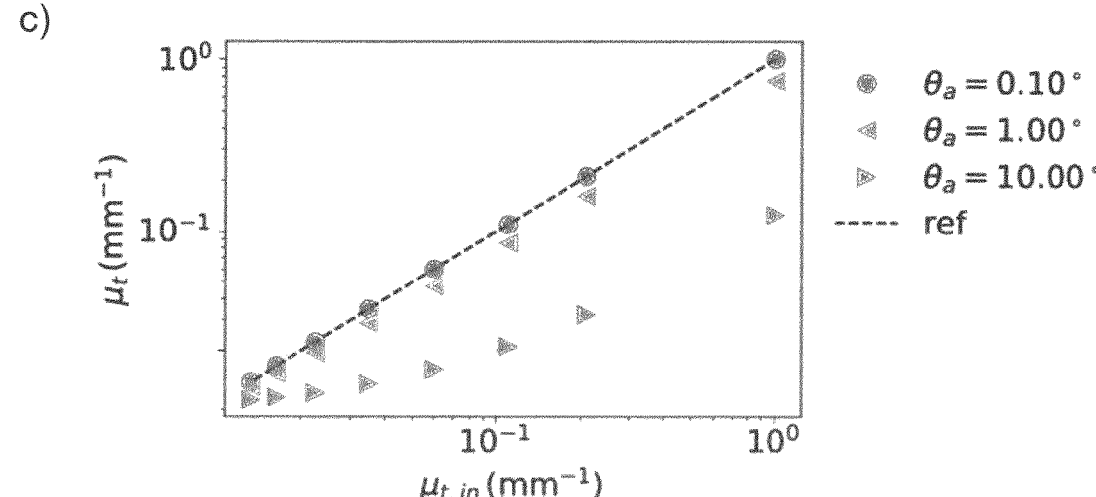
Figure 6:
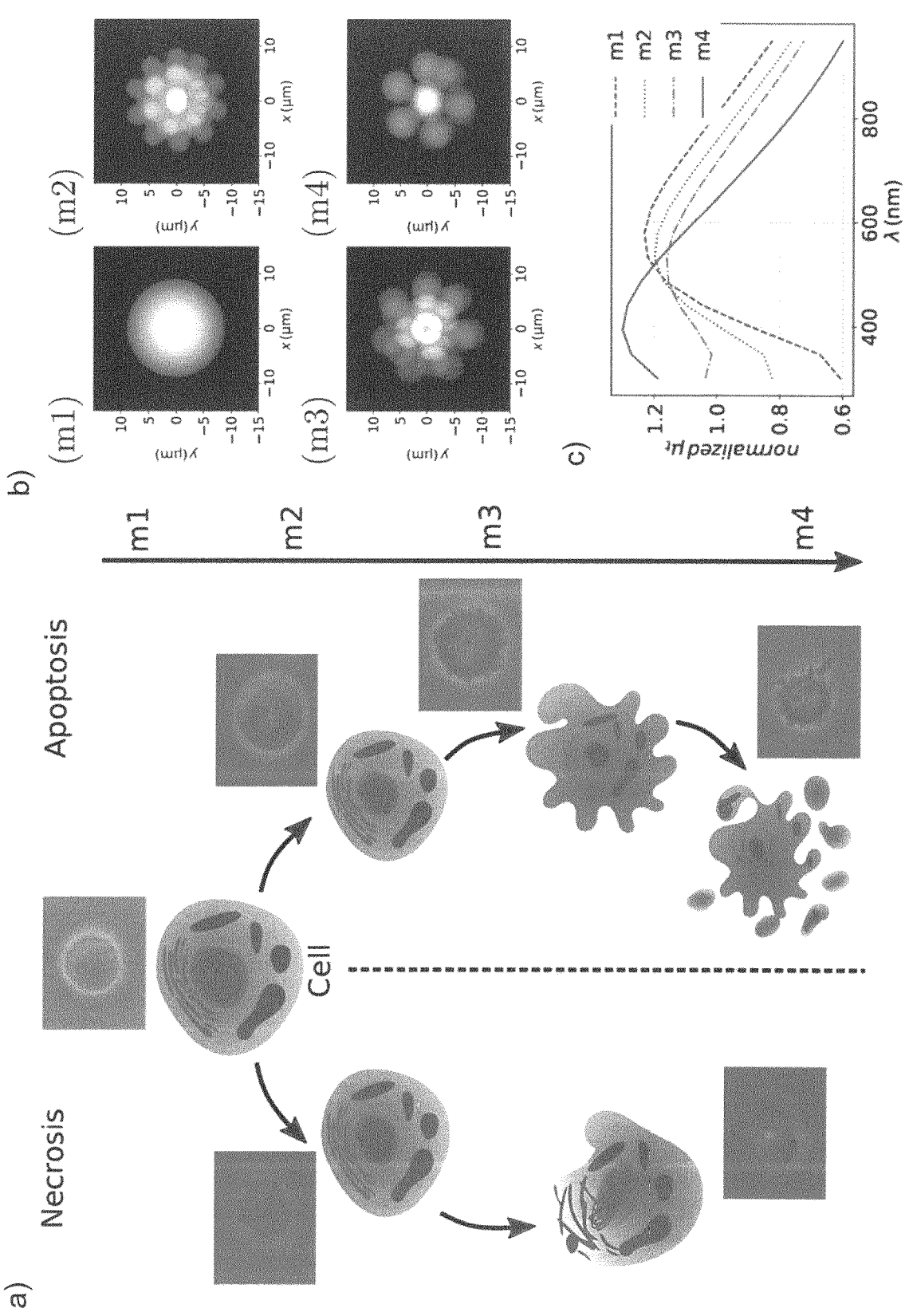
FIG. 6a shows schematics of necrotic and apoptotic cell death paths.
FIG. 6b shows microscopic cell models used for theoretical calculation.
FIG. 6c shows extinction spectra calculated based on the cell models of FIG. 6b.

This falsely detected scattered light leads to a restrained sensitivity of the transmission signal with respect to changes in the scattering behavior of the turbid sample (e.g. cell suspension), and in addition, it would mix absorption and scattering in a nonlinear way (see, e.g., FIG. 3c). A transmission measurement with a reduced $\theta_a$ (collimated transmission), however, results in a reliable determination of the extinction coefficient $\mu_t$, even for highly anisotropic scattering particles such as biological cells (also CHO-K1). In addition, the scattering cross section of biological cells in the VIS-NIR spectral range is mostly much bigger than the absorption (see FIG. 8) so that $\mu_t$ approximately corresponds to $\mu_s$. This means that the collimated transmission in principle directly probes the scattering spectrum. The relative slope of this spectrum is very sensitive to morphological changes of the scattering structures (correlation with viability, see FIG. 6), whereas the absolute value of extinction is linearly correlated to the concentration of the scattering structures (absolute or total cell count).

UV-Vis transmission measurements are technically related to the measuring principle of collimated transmission and are used as standard in fermentations. In these measurements, however, commercially available transmission probes are used, which have a combined acceptance angle (combined from divergence of irradiation and acceptance angle of detection) of >10°. In the case of clear analytes (no scattering), the measured transmission is independent of the acceptance angle, but in turbid samples such as biological cell suspensions, an enlarged acceptance angle leads to a non-specific detection of light of different transmission lengths. This leads to a nonlinear mixture of absorption and scattering of the analyte, which makes model development based on multivariate methods very complex. By reducing the acceptance angle, this nonlinear mixture can be reduced and at a sufficiently small angle, the extinction coefficient can be determined from the transmission measurement. This represents a linear sum of absorption and scattering, which makes model development possible.

In FIGS. 3a and 3b, the difference between a simple transmission measurement with a combined or effective acceptance angle of 10° and a collimated transmission measurement (combined acceptance angle of 0.1° is illustrated for a typical CHO-K1 cell suspension based on a model calculation. It can be clearly seen that both a change in the concentration (FIG. 3a, C1 or C2) and a change in the anisotropy of the scattering (FIG. 3b, g-factor) leads to transmission spectra which differ from a reference (ref), if the transmission spectra are recorded with a large effective acceptance angle $\theta_a$. In comparison, the spectra recorded with a small effective acceptance angle $\theta_a$ always match the reference.

In particular, FIG. 3a shows simulated CHO-K1 extinction spectra for two different $\theta_a$ and three different anisotropy factors g. In case of a morphological change of the biological cells, both the scattering phase function and the extinction coefficient will change and therefore also the optical anisotropy factor of the cell suspension. In case of bad collimation (here e.g. $\theta_a=10°$ a change in g is also influencing the spectra so that phase function and extinction coefficient are mixed in the transmission signal. The collimated transmission with $\theta_a<1$ on the contrary guarantees the exact determination of $\mu_r$.

FIG. 3b shows simulated transmission spectra as expected for CHO-K1 cells in a typical bio process, for two different $\theta_a$ and three different anisotropy factors g. Only for small acceptance angles (0.1°), the spectrum is decoupled from a change in anisotropy and hence suitable for a reproducible quantification of viable cell count.

Up to now, model development or calibration was difficult due to the nonlinearity of light scattering (see FIGS. 3a and 3b). In particular, conventional UV/Vis transmission measurements do not contain quantitative information on extinction and/or isotropy of scattering, and thus do not allow conclusions about the viability. Within the present invention, however, it has been found that the quantitative measurement of the extinction coefficient by means of collimated transmission allows to quantify the light scattering of the cells, which dominates in the VIS and NIR for typical cell suspensions against absorption anyway, and to quantify the model development based on the scattering spectra.

Collimated transmission as used within the present invention is a special kind of transmission spectroscopy with a very small effective acceptance angle $\theta_a$ compared to commercially available transmission probes. The effective acceptance angle is defined as the sum of the beam divergence and the acceptance angle of the detection. Within the present invention, the influence of $\theta_a$ onto the transmission signal was simulated using the Monte Carlo method for calculating the light propagation through a slab of scattering and absorbing media, comparable to a CHO-K1 cell suspension (cf. FIG. 8).

FIG. 3c shows the influence of $\theta_a$ on the determination of the extinction coefficient $\mu_r$, where $\mu_{t,in}$ denotes the actual extinction coefficient used in the simulation. In particular, FIG. 3c shows simulated transmission values for different $\theta_a$ and extinction coefficients $\mu_t$ with an anisotropy factor of 0.98. Only a small acceptance angle $\theta_a$ results in a linear behavior between the extinction coefficient $\mu_t$, which would have been measured, and the actual extinction $\mu_{t,in}$.

In case of perfect collimation ($\theta_a=0°$), only the part of light, which was neither absorbed nor scattered would be measured. In reality, the minimum divergence of a beam with width w and wavelength $\lambda$ is limited by $$\theta_{min} \approx \frac{\lambda}{2w}$$

due to the resolution limit of electromagnetic radiation. However, it is possible to tune this angle by the optical design of the transmission probe. These different designs have already been described above in connection with FIG. 2b.

Figure 4:
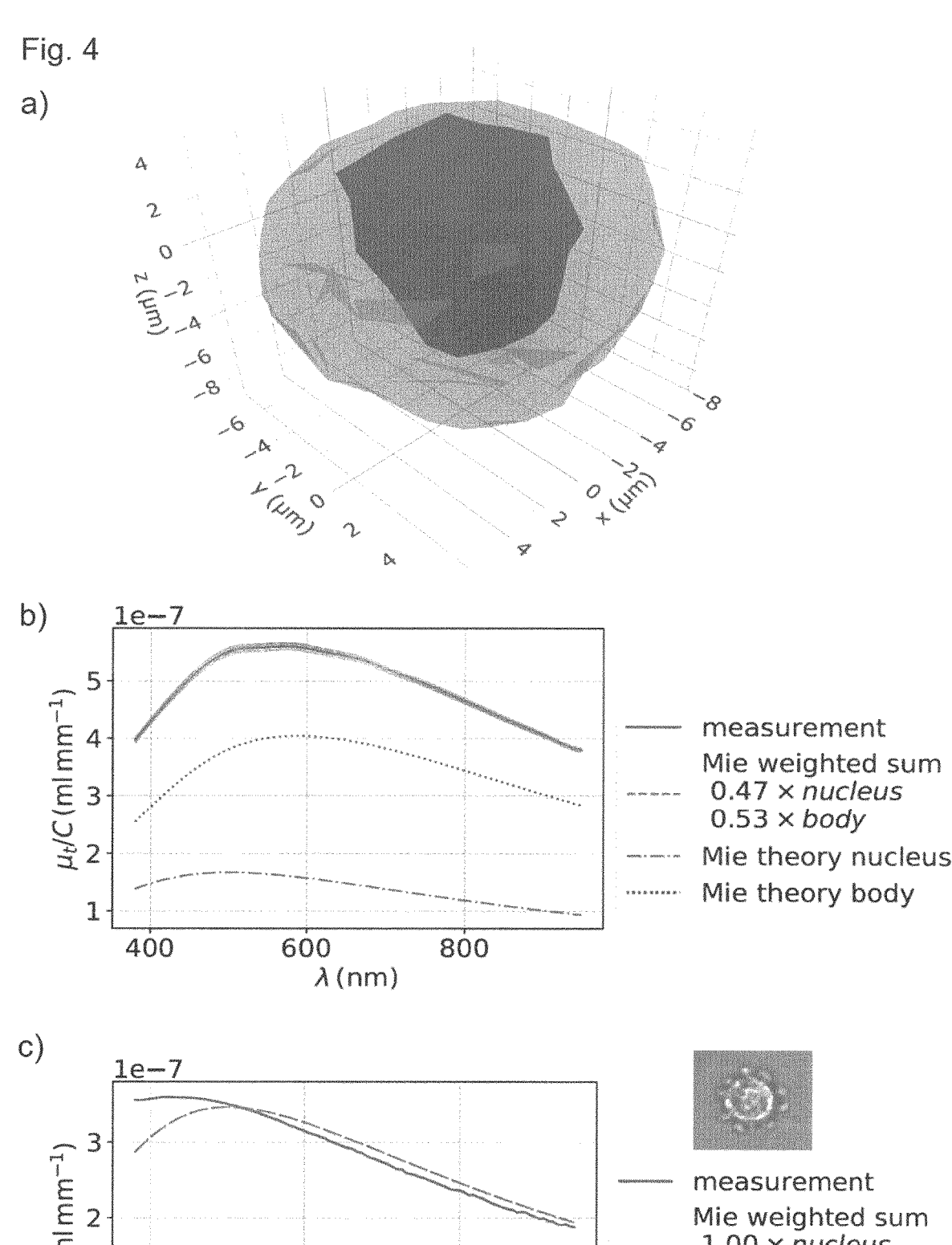

In particular, the new approach according to the present invention is based on the direct change of the measurement signal due to the different angle-dependent scattering of the light and the absolute scattering cross-section of the biological cells depending on their morphology. Healthy cells or bacteria have a typical molecular and geometrical structure which entails a very specific refractive index distribution. If this distribution could be precisely determined for a biological cell, it would be possible in principle to accurately predict the scattering behavior with the help of numerical solutions of the Maxwell's equations. The BMBF project "Multispek" has shown that an exact knowledge of the refractive index distribution of each individual cell is not necessary, but that rather the scattering behavior can be reduced to the most important structures by means of a simultaneous measurement of a large number of cells. Thus, in view of CHO-K1 cells, their scattering behavior can be described almost completely by the nucleus and the entire cell body. To show this for the CHO-K1 cells, the morphology of about 40 cells was determined with the help of a laser scanning microscope, and the mean diameter of the nucleus as well as the entire cells was determined. Such a measurement is presented in FIG. 4a showing a 3D model of CHO-K1 cells consisting of nucleus and cell body. The geometry was determined based on measurements of fluorescence-colored cells using a laser scanning microscope.

Based on this data, the scattering behavior of the CHO-K1 cells was calculated using Mie theory solutions and compared with measurements. As shown in FIG. 4b, the theoretical model (based on first-principles) fits very well with measurements of viable cells. This spectral signature, conditioned by the scattering behavior (extinction coefficient $\mu_r$) can be seen as a kind of "fingerprint" for viable CHO-K1 cells. A change in the cultivation environment of the cells (for example, flow velocity, temperature, nutrient content and/or concentration of metabolites, etc.) usually leads to an adaptation and associated morphological change of the cells. Within the present invention, this was shown both by a lack of nutrient (no fresh nutrient medium) and by the addition of a cytostatic agent (valinomycine which destroys the membrane potential of the cell) to shaking cultures.

In FIG. 4c a significant discrepancy between the analytical model and the measurement is shown. The reason for this is a morphological change similar to the formation of vesicles on the cell membrane as shown in the inlet of FIG. 4c. The cell shown in this inlet resided in a matrix added with trypan blue, which, however, has not led yet to a coloration. The new method according to the present invention is therefore even more selective than the currently established coloring with trypan blue.

Figure 5:
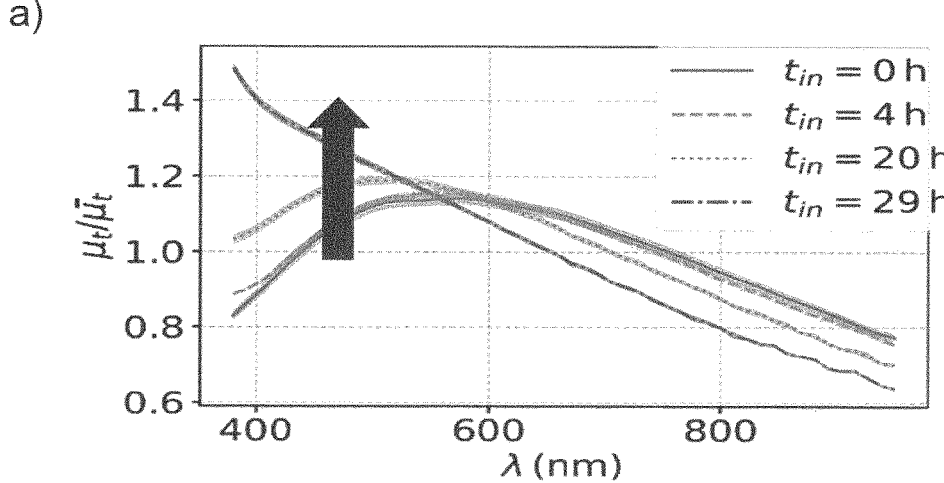
FIG. 5a shows standardized extinction spectra of CHO-K1 cells from shaking culture at incubation with the cytostatic Valinomycin with a concentration of 0.5 µMol for 0, 4, 20 and 29 hours.
FIG. 5b shows absolute extinction spectra of CHO-K1 cells as in FIG. 3a together with modelled extinction spectra.
Figure 5:
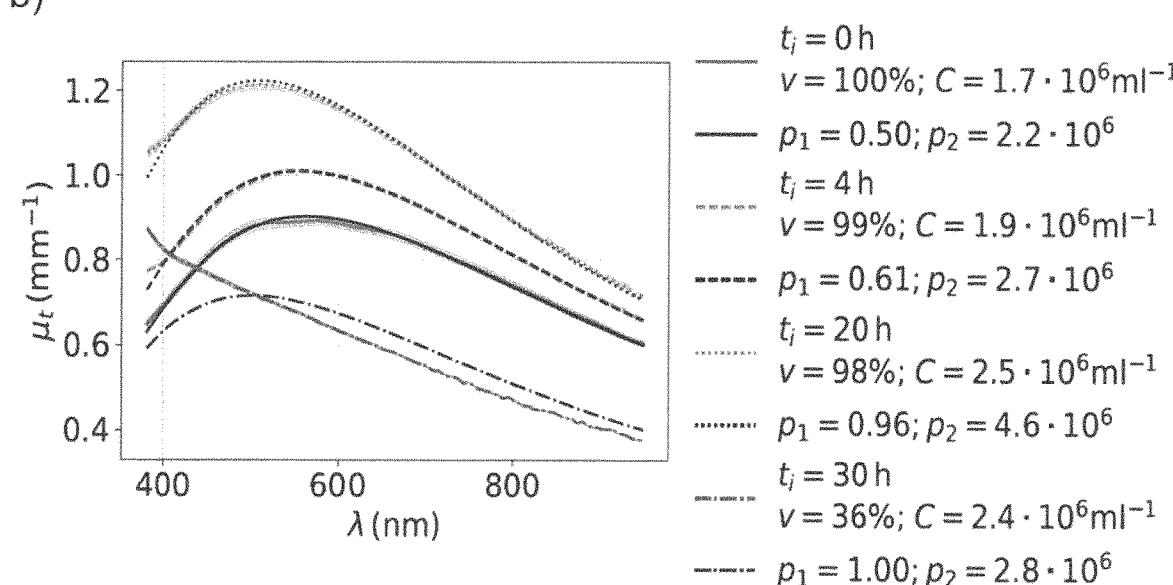

FIG. 5a shows standardized extinction spectra of CHO-K1 cells from shaking culture at incubation with the cytostatic Valinomycin with a concentration of 0.5 µMol for 0, 4, 20 and 29 hours, and FIG. 5b shows absolute extinction spectra of CHO-K1 cells as in FIG. 3a together with modelled extinction spectra.

A Calibration/modeling can be done either by one of the following ways:

A) Determination of the scattering properties of morphological parameters based on first principles without the use of reference spectra, e.g. via the solution of the Maxwell's equations. For this purpose, a first approach is shown in FIG. 5b, wherein an analytical model based on the Mie theory with two model parameters p1 and p2 is used. P1 correlates with viability and p2 with cell concentration.

Figure 9:
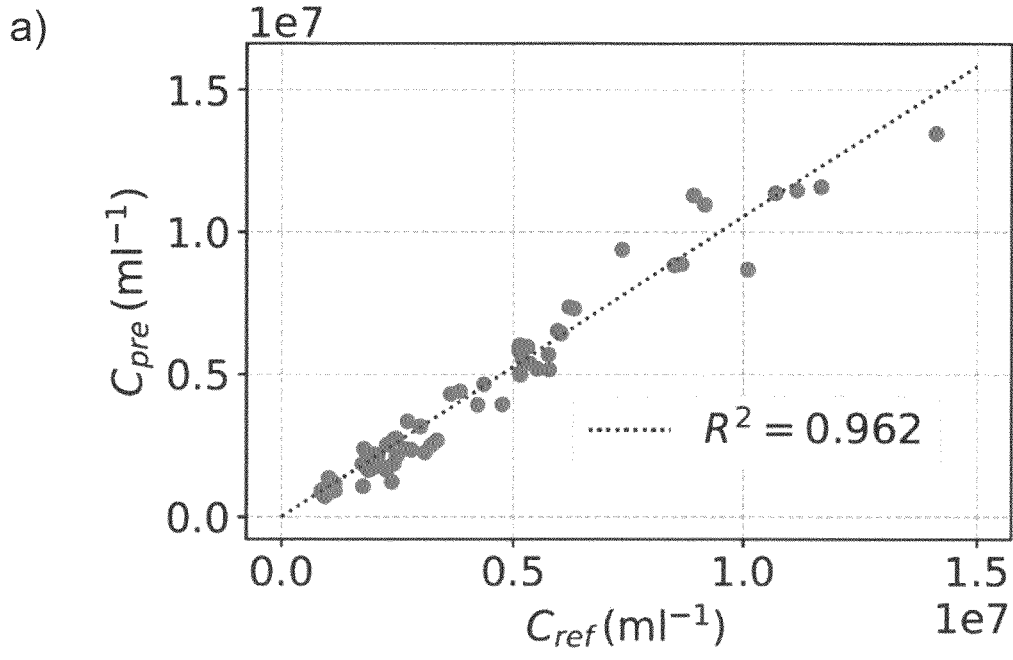
Figure 9:
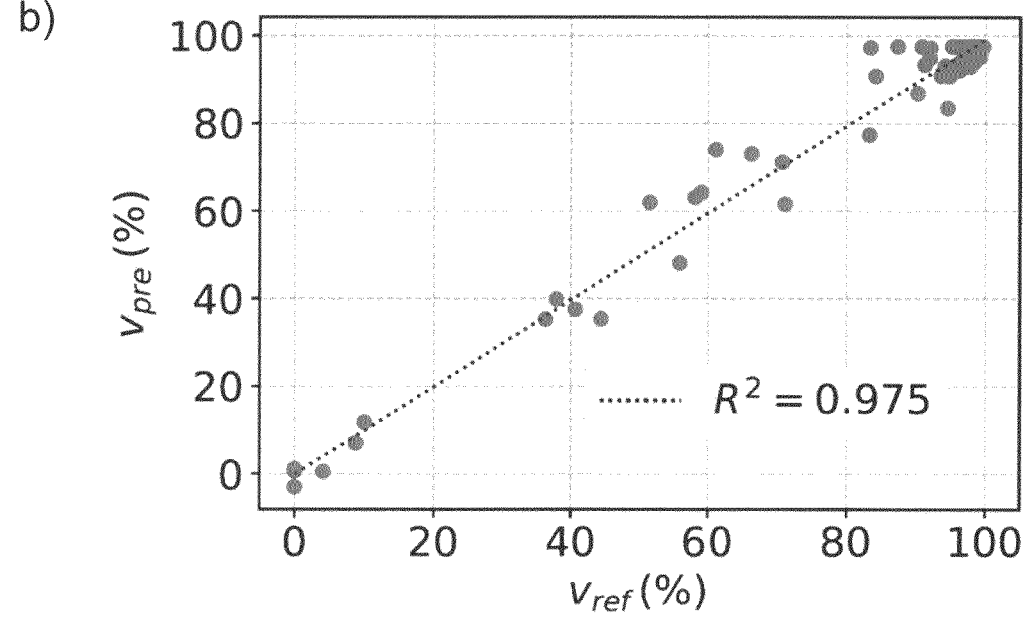

B) Determination of morphological parameters via spectra of samples with known target properties (e.g. vitality, cell concentration, etc.):

a) Determination of the target parameters by linear superposition of base spectra which have been measured once for the respective target size. For example, the extinction spectrum of a viable culture can be determined and that of an apoptotic as well as a dead cell culture can be mapped by linear superimposition of these basic states.

b) Use of a linear chemometric model based on decomposition into main components.

c) Use of nonlinear methods based on neural networks or MVDAs. In FIG. 9, a neural network based on a three-layer MLP (multilayer perceptron) was trained with a data set of 50 spectra for determining cell concentration and cell viability. The input layer consisted of 20 spectral channels.

FIG. 6a shows schematics of necrotic and apoptotic cell death paths. FIG. 6b shows microscopic cell models used for theoretical calculation. And FIG. 6c shows extinction spectra calculated based on the cell models of FIG. 6b. This is in qualitative agreement to the measurements shown in FIG. 7a.

Figure 7:
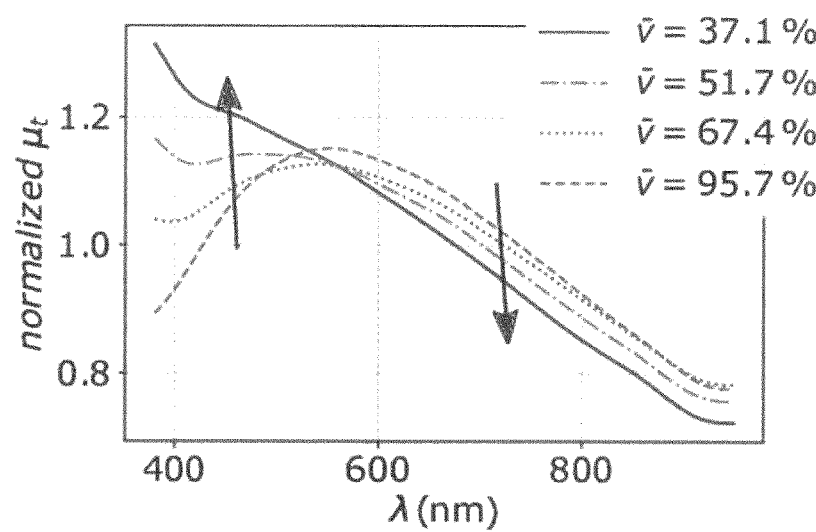
FIG. 7a shows normalized extinction coefficients from a set of 68 CHO-K1 cell suspension spectra, where each spectrum is an average over five spectra and the legend shows the averaged viability of the corresponding cell suspensions.
FIG. 7b shows scattering phase functions of a CHO-K1 cell suspension from one cultivation for a wavelength of 600 nm.
FIG. 7c shows the spectrally averaged mean cosine (dots, left axis) of the scattering phase functions from the plot in FIG. 7b, as well as the viability (triangles, right axis)
Figure 7:
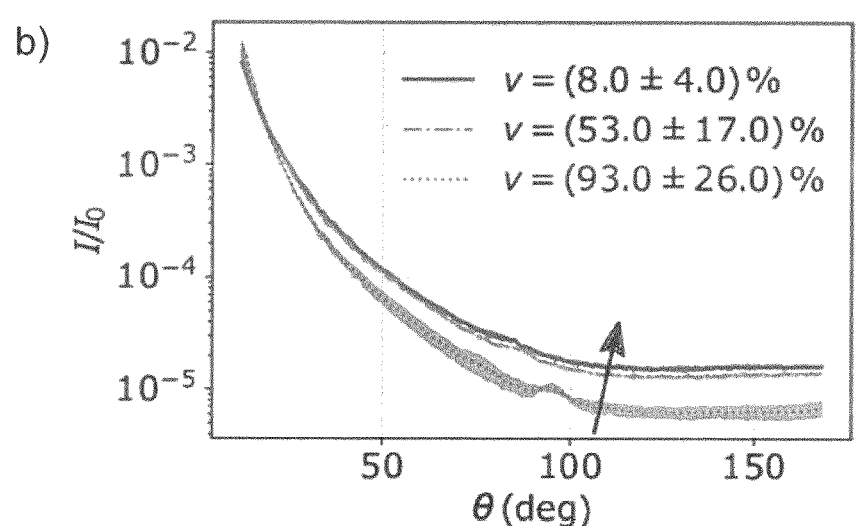
Figure 7:
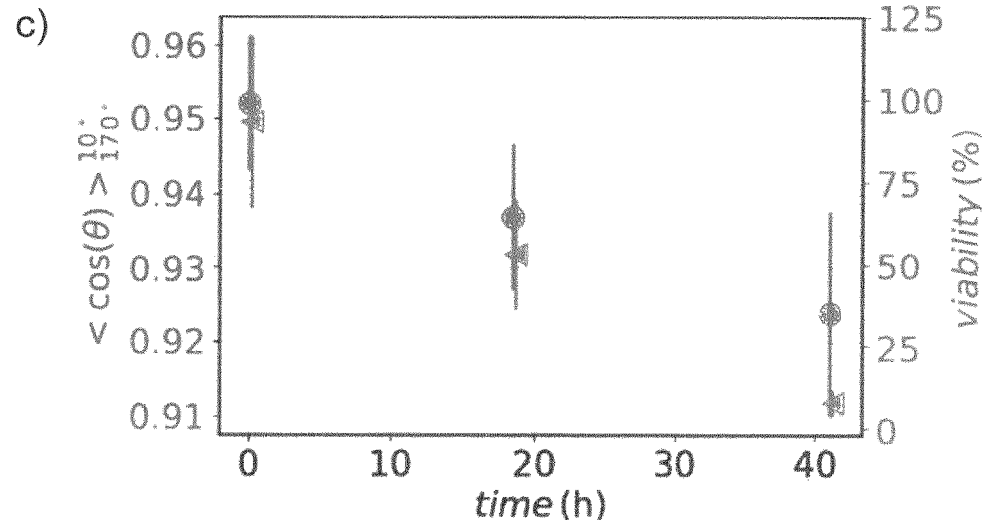

FIG. 7a shows normalized extinction coefficients from a set of 68 CHO-K1 cell suspension spectra, where each spectrum is an average over five spectra and the legend shows the averaged viability of the corresponding cell suspensions. The arrows indicate the correlation between the spectra and a decreasing viability.

FIG. 7b shows scattering phase functions of a CHO-K1 cell suspension from one cultivation for a wavelength of 600 nm. A decrease in viability is correlated to a decreasing anisotropy, as indicated by the arrow.

FIG. 7c shows the spectrally averaged mean cosine (dots, left axis) of the scattering phase functions from the plot in FIG. 7b. The decreasing anisotropy can directly be correlated with the viability (triangles, right axis).

FIG. 8a shows absorption spectra of a CHO-K1 cell suspension from integrating sphere measurements.

FIG. 8b shows a reduced scattering spectrum (left axis) of a CHO-K1 cell suspension from integrating sphere measurements, as well as the extinction coefficient $\mu_t$ (right axis) of the same sample measured with collimated transmission.

FIG. 8c shows the anisotropy factor $$g = 1 - \frac{\mu_s'}{\mu_t - \mu_a}$$

calculated from the integrating sphere and collimated transmission measurements shown in FIGS. 8a) and 8b). The highly anisotropic scattering behavior ($\bar{g} > 0.99$) of the CHO-K1 cell suspension is shown, moreover $\mu_t \gg \mu_a$ indicates that $\mu_t \approx \mu_s$.

FIG. 9a shows an absolute (or total) cell count and FIG. 9b shows the predicted viability from 75% of all CHO-K1 spectra acquired during a study carried out within the present invention. The classification is based on a multilayer perceptron (MLP) with one input, one output and one hidden layer with four perceptrons. Training was done with 25% of total data.

A device or sensor according to the present invention, i.e. a device or sensor being based on collimated transmission, allows for the inline monitoring of cell parameters in a bioprocess. The full capabilities are particularly exploited in the control of non-bleed and bleed perfusion processes. In both cases, the sensor may be integrated in the bioreactor and detect cell parameters inline in real-time. As illustrated in FIGS. 10 and 11, which are further described below, the present invention may advantageously be used in these upstream bioprocesses, thereby resulting in an easier handling and allowing an effective and reliable inline monitoring of cell parameters.

FIG. 10 shows a flow diagram of a non-bleed perfusion process according to an example. Here, the sensor 100 is used for the control of nutrient levels. By means of inline measurement of cell parameters, the required nutrient level can be calculated based on a known cell specific nutrient consumption rate and a resulting cell specific perfusion rate ($c_{spr}$). This allows for the adjustment of feed pump speed or respectively the start and stop of the feed pump. In particular, in a step S1, the process starts. In a step S2, it is checked whether a process end is reached. If the process end is reached, the process is stopped in step S3a. If the process end has not been reached, a measurement of at least one cell parameter (such as viability, viable cell count and/or total cell count) is carried out in a step S3b with a cell parameter device or sensor 100 according to the present invention. In a step S4, based on the measurements of the at least one cell parameter in step S3b, it is checked whether a required nutrient level is too low, i.e., whether the nutrient level is below a specified (predetermined or determinable) nutrient level threshold. If the nutrient level is too low, i.e., if the nutrient level is below the specified nutrient level threshold, a feed pump is started and/or a feed pump speed of the feed pump is increased. If the nutrient level is sufficiently high, i.e., if the nutrient level is equal to or above the specified nutrient level threshold, the feed pump is stopped and/or the feed pump speed is decreased. After any one of steps S5a and S5b has been carried out, the process continues again with step S2.

FIG. 11 shows a flow diagram of a perfusion process with cell bleed according to an example. This example shows the control of the cell bleed based on the inline detection of cell parameters based on the collimated transmission sensor. In particular, in a step S10, the process starts. In a step S20, it is checked whether a process end is reached. If the process end is reached, the process is stopped in step S30a. If the process end has not been reached, a measurement of at least one cell parameter (such as viability, viable cell count and/or total cell count) is carried out in a step S30b with a cell parameter device or sensor 100 according to the present invention. In a step S40, based on the measurements of the at least one cell parameter in step S30b, it is checked whether the at least one cell parameter is higher than a specified set point. If the at least one cell parameter is equal to or below the set point, a cell bleed pump is stopped and/or a cell bleed pump speed of the cell bleed pump is decreased. If the at least one cell parameter is higher than the set point, the cell bleed pump is started and/or the cell bleed pump speed of the cell bleed pump is increased. After any one of steps S50a and S50b has been carried out, the process continues again with step S20.

Applicant: Sartorius Stedim Biotech GmbH et al.

"Device and method for determining a viability and/or a cell count of biological cells in a cell suspension culture by means of collimated transmission"

LIST OF REFERENCE NUMERALS

1 illumination source
2 illumination fiber
5 illumination lens (illumination focusing optics)
5*a* lens (refractive focusing unit)
5*b* parabolic mirror (reflective focusing unit)
6 sample
7 container/cuvette (sample volume)
8 aperture
9 detection lens (detection focusing optics)
12 detection fiber
13 detection unit
14 illumination beam collimation unit
15 transmission beam focusing unit
17 core of fiber
18 cladding of fiber
19 outer shell
20 light switch
100 device (sensor)
d inner diameter of fiber
$d_1$ inner diameter of illumination fiber
$d_2$ inner diameter of detection fiber
D distance
f focal length
focus length of illumination focusing optics
$f_2$ focus length of detection focusing optics
L transmission length (length of sample volume or container)
r diameter of aperture
$\theta_1$ maximal illumination beam divergence angle
$\theta_2$ maximal transmission beam detection angle
$\theta_a$ effective (combined) acceptance angle

The invention claimed is:

1. A device for determining a viability and/or a cell count of biological cells in a cell suspension culture by means of collimated transmission, comprising:
an illumination source for generating an electromagnetic illumination beam;
beam manipulation means for collimating the illumination beam; and
a detection unit for detecting an electromagnetic transmission beam being a portion of the collimated illumination beam which has been transmitted through a sample of the cell suspension culture,
wherein the beam manipulation means are configured to manipulate the illumination beam and/or the transmission beam such that an effective acceptance angle $\theta_a$ of the collimated transmission is equal to or below a specified threshold value, wherein the effective acceptance angle $\theta_a$ is defined as the sum of:
a maximal illumination beam divergence angle $\theta_1$, of the collimated electromagnetic illumination beam, and
a maximal transmission beam detection angle $\theta_2$ of the transmission beam.

2. The device according to claim 1, wherein:
the beam manipulation means are configured to collimate the illumination beam such that the illumination beam has a divergence angle of less than 1.5 degrees; and/or
the beam manipulation means are configured to manipulate the transmission beam such that the transmission beam has a divergence angle of less than 1.5 degrees, and/or
the beam manipulation means are configured to manipulate the illumination beam and/or the transmission beam such that an effective acceptance angle $\theta_a$ of the collimated transmission is equal to or less than 3 degrees.

3. The device according claim 1, wherein the beam manipulation means comprise at least one of the following:
an illumination fiber for guiding the illumination beam;
an illumination beam collimation unit for collimating the illumination beam;
a transmission beam focusing unit for focusing the transmission beam; and
a detection fiber for guiding the transmission beam to the detection unit.

4. The device according to claim 3, wherein the illumination fiber and/or the detection fiber have a numerical aperture smaller than 0.02.

5. The device according to claim 3, wherein the illumination beam collimation unit and/or the transmission beam focusing unit comprises at least one of the following:
an aperture, a refractive focusing unit, and a reflective focusing unit.

6. The device according to claim 1, wherein:
the beam manipulation means comprise an illumination beam collimation unit, the illumination beam collimation unit comprising an illumination fiber and an illumination focusing optics,
wherein the illumination fiber is configured to guide the illumination beam to the illumination focusing optics,
wherein the illumination focusing optics is arranged between an end of the illumination fiber and the sample such that a distance between the end of the illumination fiber and the illumination focusing optics is equal to a focal length ($f_1$) of the illumination focusing optics; and/or
the beam manipulation means comprise a transmission beam focusing unit, the transmission beam focusing unit comprising a detection focusing optics and a detection fiber,
wherein the detection fiber is configured to guide the transmission beam to the detection unit,
wherein the detection focusing optics is arranged between the sample and an end of the detection fiber such that a distance between the detection focusing optics and the end of the detection fiber is equal to a focal length ($f_2$) of the detection focusing optics.

7. The device according to claim 6, wherein the effective acceptance angle $\theta_a$ is given by the following equation:

$$\theta_a = \tan^{-1}\left(\frac{d_1}{f_1}\right) + \tan^{-1}\left(\frac{d_2}{f_2}\right).$$

where $d_1$ denotes an inner diameter of the illumination fiber (2), $d_2$ an inner diameter of the detection fiber, $f_1$ the focal length of the illumination focusing optics, and $f_2$ the focal length of the detection focusing optics.

8. The device according to claim 1, wherein:
the illumination source is a polychromatic light source and the detection unit is a spectrometer; or
the frequency of the illumination source is tuneable and the detection unit is a broadband detector or a tunable monochromatic detector.

9. The device according to claim 1, further comprising:
an evaluation unit for determining the viability, a viable cell count and/or a total cell count of the biological cells based on the detected transmission beam, wherein in particular, the evaluation unit is configured to determine an extinction spectrum based on the detected transmission beam and to determine the viability, the viable cell count and/or the total cell count based on the extinction spectrum by comparing the determined extinction spectrum with reference extinction spectra.

10. The device according to claim 9, wherein the reference extinction spectra are modelled based on first principles by solving Maxwell's equations and/or using Mie's theory.

11. The device according to claim 9, wherein the reference extinction spectra are obtained by measurements carried out on samples with known properties.

12. The device according to claim 1, comprising a sample container for containing a sample of the cell suspension culture.

13. A bioreactor comprising the device according to claim 1.

14. A method for determining a viability and/or a cell count of biological cells in a cell suspension culture by means of a collimated transmission, the method comprising:
    illuminating a sample of the cell suspension culture with a collimated electromagnetic illumination beam;

detecting an electromagnetic transmission beam being a portion of the collimated electromagnetic illumination beam which has been transmitted through the sample of the cell suspension culture; and determining the viability and/or the cell count of the biological cells based on the detected transmission beam, wherein the illumination beam and/or the transmission beam are/is manipulated such that an effective acceptance angle $\theta_a$ of the collimated transmission is equal to or below a specified threshold value, and wherein the effective acceptance angle $\theta_a$ is defined as the sum of:

a maximal illumination beam divergence angle $\theta_1$ of the collimated electromagnetic illumination beam, and a maximal transmission beam detection angle $\theta_2$ of the transmission beam.

15. The method of claim 14, wherein the collimated transmission is performed by a device according to claim 1.

* * * * *